US011851500B2

(12) United States Patent
Codington et al.

(10) Patent No.: US 11,851,500 B2
(45) Date of Patent: Dec. 26, 2023

(54) ANTIBODIES USEFUL FOR DETECTION OF HUMAN CARCINOMA ANTIGEN

(71) Applicant: Emory University, Atlanta, GA (US)

(72) Inventors: John Codington, Atlanta, GA (US); Priscilla Davidson, Marietta, GA (US); Priscilla Agbenyefia, Dayton, OH (US)

(73) Assignee: Emory University, Atlanta, GA (US)

( * ) Notice: Subject to any disclaimer, the term of this patent is extended or adjusted under 35 U.S.C. 154(b) by 112 days.

(21) Appl. No.: 17/208,977

(22) Filed: Mar. 22, 2021

(65) Prior Publication Data

US 2021/0230297 A1 Jul. 29, 2021

Related U.S. Application Data

(62) Division of application No. 16/285,805, filed on Feb. 26, 2019, now Pat. No. 10,975,164.

(60) Provisional application No. 62/635,206, filed on Feb. 26, 2018.

(51) Int. Cl.

| | |
|---|---|
| ***C07K 16/30*** | (2006.01) |
| ***C12N 15/85*** | (2006.01) |
| ***C07K 16/46*** | (2006.01) |
| ***G01N 33/574*** | (2006.01) |
| ***C07K 16/40*** | (2006.01) |
| ***C07K 16/00*** | (2006.01) |
| ***C07K 16/42*** | (2006.01) |

(52) U.S. Cl.

CPC .......... *C07K 16/3092* (2013.01); *C07K 16/00* (2013.01); *C07K 16/40* (2013.01); *C07K 16/4241* (2013.01); *C07K 16/46* (2013.01); *C12N 15/85* (2013.01); *G01N 33/574* (2013.01); *C12N 2015/8518* (2013.01)

(58) Field of Classification Search

CPC .... C07K 16/3092; C07K 16/00; C07K 16/40; C07K 16/4241; C07K 16/46; C07K 16/30; C12N 15/85; C12N 2015/8518; G01N 33/574

See application file for complete search history.

(56) References Cited

U.S. PATENT DOCUMENTS

| | | | | |
|---|---|---|---|---|
| 4,837,171 | A | 6/1989 | Codington | |
| 5,545,532 | A | 8/1996 | Codington | |
| 5,693,763 | A * | 12/1997 | Codington | C07K 14/4748 530/387.5 |
| 5,808,005 | A | 9/1998 | Codington | |
| 8,658,172 | B2 | 2/2014 | Reinhardt | |
| 2005/0272102 | A1 * | 12/2005 | Mauck | G01N 33/57434 435/7.23 |

OTHER PUBLICATIONS

Brodeur BR, Hamel J, Tackaberry E. Anti-idiotype antibodies for the diagnosis of infectious diseases. Can J Infect Dis. Nov. 1992;3(6):319-20. doi: 10.1155/1992/189281. PMID: 22346409; PMCID: PMC3250736. (Year: 1992).*

Codington et al. Glycoprotein Coat of the TA3 Cell. Isolation and Partial Characterization of a Sialic Acid Containing Glycoprotein Fraction, Biochemistry, 1972, 1(14):2559-64.

Codington et al. Epiglycanin—a carcinoma-specific mucin-type glycoprotein of the mouse TA3 tumour, Glycobiology, 1992, 2(3):173-80.

Codington et al. Immunologic Quantitation of the Carcinoma Specific Human Carcinoma Antigen in Clinical Samples, Cancer, 2002, 94(3):803-13.

Palma et al. The human epithelial carcinoma antigen recognized by monoclonal antibody AE3 is expressed on a sulfoglycolipid inaddition to neoplastic mucins, Biochem Biophys Res Commun, 2011, 408(4):548-52.

Yi et al. Mucin 21/Epiglycanin Modulates Cell Adhesion, J Biol Chem. 2010, 285(28): 21233-21240.

* cited by examiner

*Primary Examiner* — Hong Sang
*Assistant Examiner* — Sung Min Yoon
(74) *Attorney, Agent, or Firm* — Emory Patent Group

(57) ABSTRACT

This disclosure relates to diagnostic assays useful to detect a carcinoma from a sample and antibodies or binding fragments thereof useful in the diagnostic tests. In certain embodiments, this disclosure relates to antibodies or fragments that bind HCA, epiglycanin, and/or fragments thereof. In certain embodiments, this disclosure relates to anti-idiotypic antibodies or fragments that bind the variable regions of antibodies that bind HCA and/or epiglycanin.

13 Claims, 3 Drawing Sheets

Specification includes a Sequence Listing.

(SEQ ID NO: 17) METHSQVFVYMLLWLSGVEGGIVMTQSHKFMSTSIGDRVS
ITCKASQDVGTAVAWYQQKPGQSPKLLIFWASTRHTGVPDRFTGSGSGTDFTLT
ISNVQSEDLADYFCQHYINYPLTFGAGTKLELKRADAAPTVSIFPPSSEQLTSG
GASVVCFLNNFYPKDINVKWKIDGSERQNGVLNSWTDQDSKDSTYSMSSTLTLT
KDEYERHNSYTCEATHKTSTSPIVKSFNRGEC

```
  1 atggagacac attctcaggt ctttgtatac atgttgctgt ggttgtctgg tgttgaagga
 61 ggcattgtga tgacccagtc tcacaaattc atgtccacat caataggaga cagggtcagc
121 atcacctgca aggccagtca ggatgtgggt actgctgtgg cctggtatca acagaaacca
181 gggcaatctc ctaaactact gatttctgg gcatccaccc ggcacactgg agtccctgat
241 cgcttcacag gcagtggatc tgggacagat ttcactctca ccattagcaa tgtgcagtct
301 gaagacttgg cagattattt ctgtcagcat tatatcaact atcctctcac gttcggtgct
361 gggaccaagc tggagctgaa acgggctgat gctgcaccaa ctgtatccat cttcccacca
421 tccagtgagc agttaacatc tggaggtgcc tcagtcgtgt gcttcttgaa caacttctac
481 cccaaagaca tcaatgtcaa gtggaagatt gatggcagtg aacgacaaaa tggcgtcctg
541 aacagttgga ctgatcagga cagcaaagac agcacctaca gcatgagcag caccctcacg
601 ttgaccaagg acgagtatga acgacataac agctatacct gtgaggccac tcacaagaca
661 tcaacttcac ccattgtcaa gagcttcaac aggggagagt gttga (SEQ ID NO: 18)
```

FIG. 3A (SEQ ID NO: 19) MEWCWVFLFLLSVTAGVHSQVQLQQSGAELVKPGASVKLS
CKASGYTFTEYTIHWVKQRSGQGLEWIGWFYPGSGSIKYNEKFKDKATLTADKY
SSTVYMELSSLTSEDSAVYFCARGGYYDSFDNWGQGTTLTVSSESQSFPNVFPL
VSCESPLSDKNLVAMGCLARDFLPSTISFTWNYQNNTEVIQGIRTFPTLRTGGK
YLATSQVLLSPKSILEGSDEYLVCKIHYGGKNRDLHVPIPAVAEMNPNVNVFVP
PRDGFSGPAPRKSKLICEATNFTPKPITVSWLKDGKLVESGFTTDPVTIENKGS
TPQTYKVISTLTISEIDWLNLNVYTCRVDHRGLTFLKNVSSTCAASPSTDILTF
TIPPSFADIFLSKSANLTCLVSNLATYETLNISWASQSGEPLETKIKIMESHPN
GTFSAKGVASVCVEDWNNRKEFVCTVTHRDLPSPQKKFISKPNEVHKHPPAVYL
LPPAREQLNLRESATVTCLVKGFSPADISVQWLQRGQLLPQEKYVTSAPMPEPG
APGFYFTHSILTVTEEEWNSGETYTCVVGHEALPHLVTERTVDKSTGKPTLYNV
SLIMSDTGGTCY

```
  1 atggaatggt gctgggtctt tctcttcctc ctgtcagtaa ctgcaggtgt ccactcccag
 61 gtccaactgc agcagtctgg agctgagctg gtgaaacccg gggcatcagt gaagctgtcc
121 tgtaaggctt ctggctacac cttcactgaa tatactatac actgggtaaa gcagaggtct
181 ggacagggtc ttgaatggat tgggtggttt taccctggaa gtggtagtat aaagtataat
241 gagaaattca aggacaaggc cacattgact gcggacaaat actccagcac agtctatatg
301 gaacttagta gcttgacatc tgaagactct gcggtctatt tctgtgcaag agggggctac
361 tatgattctt ttgacaactg gggccaaggc accactctca cagtctcctc agagagtcag
421 tccttcccaa atgtcttccc cctcgtctcc tgcgagagcc ccctgtctga taagaatctg
481 gtggccatgg gctgcctagc ccgggacttc ctgcccagca ccatttcctt cacctggaac
541 taccagaaca acactgaagt catccagggt atcagaacct tcccaacact gaggacaggg
601 ggcaagtacc tagccacctc gcaggtgttg ctgtctccca agagcatcct tgaaggttca
661 gatgaatacc tggtatgcaa aatccactac ggaggcaaaa acagagatct gcatgtgccc
```

(SEQ ID NO: 20)

FIG. 3B (SEQ ID NO: 21) MDMMVLAQFLAFLLLWFPGARCDILMTQSPSSMSVSLGDT
VSITCHASQGISGNIGWLQQKPGKSFKGLIYHGTNLEDGVPSRFSGSGSGADYS
LTISSLESEDFADYYCVQYIQFPFTFGGGTKLEIKRADAAPTVSIFPPSSEQLT
SGGASVVCFLNNFYPKDINVKWKIDGSERQNGVLNSWTDQDSKDSTYSMSSTLT
LTKDEYERHNSYTCEATHKTSTSPIVKSFNRGEC

```
  1 atggacatga tggtccttgc tcagtttctt gcattcttgt tgctttggtt tccaggtgca
 61 agatgtgaca tcctgatgac ccaatctcca tcctccatgt ctgtatctct gggagacaca
121 gtcagcatca cttgccatgc aagtcaaggc attagcggta atatagggtg gttgcagcag
181 aaaccaggga aatcatttaa gggcctgatc tatcatggaa ccaacttgga agatggagtt
241 ccatcaaggt tcagtggcag tggatctgga gcagattatt ctctcaccat cagcagccta
301 gaatctgaag attttgcaga ttattactgt gtacagtaca ttcagtttcc gttcacgttc
361 ggagggggga ccaagctgga gataaaacgg gctgatgctg caccaactgt atccatcttc
421 ccaccatcca gtgagcagtt aacatctgga ggtgcctcag tcgtgtgctt cttgaacaac
481 ttctacccca aagacatcaa tgtcaagtgg aagattgatg gcagtgaacg acaaaatggc
541 gtcctgaaca gttggactga tcaggacagc aaagacagca cctacagcat gagcagcacc
601 ctcacgttga ccaaggacga gtatgaacga cataacagct atacctgtga ggccactcac
661 aagacatcaa cttcacccat tgtcaagagc ttcaacaggg gagagtgttg a
```

(SEQ ID NO: 22)

FIG. 4A (SEQ ID NO: 23) MGWSWIFFFLLSGTAGVHCQVHLKQSGAEVVRPGASLKLS
CKASGYIFTDYYVHWAKQRPGQGLEWIARIYPGSGNTYYNEKFMVKATLTAESS
SSTAYMELSRLTSEDSAVYFCASSLYYPLDHWGQGTSVIVSSAKTTAPSVYPLA
PVCGDTTGSSVTLGCLVKGYFPEPVTLTWNSGSLSSGVHTFPAVLQSDLYTLSS
SVTVTSSTWPSQSITCNVAHPASSTKVDKKIEPRGPTIKPCPPCKCPAPNLLGG
PSVFIFPPKIKDVLMISLSPIVTCVVVDVSEDDPDVQISWFVNNVEVHTAQTQT
HREDYNSTLRVVSALPIQHQDWMSGKEFKCKVNNKDLPAPIERTISKPKGSVRA
PQVYVLPPPEEEMTKKQVTLTCMVTDFMPEDIYVEWTNNGKTELNYKNTEPVLD
SDGSYFMYSKLRVEKKNWVERNSYSCSVVHEGLHNHHTTKSFSRTPGK

```
  1 atgggatgga gctggatctt tttcttcctc ctgtcaggaa ctgcaggtgt ccactgtcag
 61 gtccacctga agcagtctgg ggctgaggtg gtgaggcctg ggcttcatt gaaactgtcc
121 tgcaaggctt ctggctacat tttcactgac tactatgtgc actgggcgaa acagcggcct
181 ggacagggac ttgagtggat tgcaaggatt tatcctggaa gtggtaatac ttactacaat
241 gagaaattca tggtcaaggc cacactgaca gcagaatcct cctccagcac tgcctacatg
301 gagctcagta ggctgacatc tgaggactct gctgtctatt tttgtgcaag cagcctctat
361 tatcctttgg accactgggg tcaaggaacc tcagtcatcg tctcctcagc caaaacaaca
421 gccccatcgg tctatccact ggcccctgtg tgtggagata caactggctc ctcggtgact
481 ctaggatgcc tggtcaaggg ttatttccct gagccagtga ccttgacctg gaactctgga
541 tccctgtcca gtggtgtgca caccttccca gctgtcctgc agtctgacct ctacaccctc
601 agcagctcag tgactgtaac ctcgagcacc tggcccagcc agtccatcac ctgcaatgtg
661 gcccacccgg caagcagcac caaggtggac aagaaaattg agcccagagg gcccacaatc
721 aagccctgtc ctccatgcaa atgcccagca cctaacctct tgggtggacc atccgtcttc
781 atcttccctc caaagatcaa ggatgtactc atgatctccc tgagccccat agtcacatgt
841 gtggtggtgg atgtgagcga ggatgaccca gatgtccaga tcagctggtt tgtgaacaac
```

(SEQ ID NO: 24)

FIG. 4B

ANTIBODIES USEFUL FOR DETECTION OF HUMAN CARCINOMA ANTIGEN

CROSS-REFERENCE TO RELATED APPLICATIONS

This application is a division of U.S. application Ser. No. 16/285,805 filed Feb. 26, 2019, which claims the benefit of U.S. Provisional Application No. 62/635,206 filed Feb. 26, 2018. The entirety of each of these applications is hereby incorporated by reference for all purposes.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy and is hereby incorporated by reference into the specification. The name of the text file containing the Sequence Listing is 15158US_ST25.txt. The text file is 24 KB, was created on Feb. 26, 2019, and is being submitted electronically via EFS-Web.

BACKGROUND

The Human Carcinoma Antigen (HCA) was reported to be a large mucin-type antigen consistently present in the blood of humans with carcinomas, cancers that originate in epithelial tissue. Epiglycanin is the mouse counterpart of HCA. See Codington, Epiglycanin—a carcinoma-specific mucin-type glycoprotein of the mouse TA3 tumour. Glycobiology, 1992, 2(3):173-80. See also U.S. Pat. Nos. 5,808,005, 5,693,763, 5,545,532.

Codington et al. report anti-idiotypic antibodies that bind to the hypervariable region of the AE3 antibody, an anti-idiotypic epiglycanin monoclonal antibody. Cancer, 2002, 94(3):803-13. Also described are anti, anti-idiotypic antibodies that bind to the hypervariable region of the anti-idiotypic antibodies. U.S. Published Patent Application No. 2005/0272102 reports methods for the diagnosis of prostate cancer by using an antibody or antigen-binding fragment thereof, which is specific for HCA in immunoassays. However, improved methods are needed.

Palma et al. report the human epithelial carcinoma antigen recognized by monoclonal antibody AE3 is expressed on a sulfoglycolipid in addition to neoplastic mucins. Biochem Biophys Res Commun. 2011, 408(4):548-52.

References cited herein are not an admission of prior art.

SUMMARY

This disclosure relates to diagnostic assays useful to detect a carcinoma from a sample and antibodies or binding fragments thereof useful in the diagnostic tests. In certain embodiments, this disclosure relates to antibodies or fragments that bind HCA, epiglycanin, and/or fragments thereof. In certain embodiments, this disclosure relates to anti-idiotypic antibodies or fragments that bind the variable regions of antibodies that bind HCA and/or epiglycanin.

In certain embodiments, this disclosure relates to antibodies or antigen binding fragments comprising complementarity determining regions (CDRs) or consensus sequences thereof, wherein the CDRs comprise the heavy and light chain CDRs of the antibodies of or derived from the XII-24 or AX2 hybridoma. In certain embodiments, antibodies or antigen binding fragments bind the variable regions of antibodies derived from the XII-24 or AX2 hybridoma.

In certain embodiments, the CDRs comprise the light chain XII-24 variable region CDRs within DILMTQSPSSMSVSLGDTVSITCHASQGIS-GNIGWLQQKPGKSFKGLIYHGTNLEDGVPS RFSGSGSGADYSLTISSLESED-FADYYCVQYIQFPFTFGGGTKLEIKR (SEQ ID NO: 1), wherein, CDR1 is QGISGN (SEQ ID NO: 3),
CDR2 is HGTN (SEQ ID NO: 4), and
CDR3 is VQYIQFPFT (SEQ ID NO: 5); and the three heavy chain XII-24 variable region CDRs within QVHLKQSGAEVVRPGASLKLSCK-ASGYIFTDYYVHWAKQRPGQGLEWIARIYPGSGNT YYNEKFMVKATLTAESSSSTAYMELSRLTSED-SAVYFCASSLYYPLDHWGQGTSVIVSS (SEQ ID NO: 2), wherein, CDR1 is GYIFTDYY (SEQ ID NO: 6),
CDR2 is IYPGSGNT (SEQ ID NO: 7), and
CDR3 is ASSLYYPLDH (SEQ ID NO: 8).

In certain embodiments, the CDRs comprise the light chain AX2 variable region CDRs within GIVMTQSHKFMSTSIGDRVSITCKASQDVGTA-VAWYQQKPGQSPKLLIFWASTRHTGVP DRFTGSGSGTDFTLTISNVQSEDLADYFCQHYINY-PLTFGAGTKLELK (SEQ ID NO: 9), wherein, CDR 1 is QDVGTA (SEQ ID NO: 11),
CDR2 is WAST (SEQ ID NO: 12), and
CDR3 is QHYINYPLT (SEQ ID NO: 13); and the three heavy chain AX2 variable region CDRs within QVQLQQSGAELVKPGASVKLSCK-ASGYTFTEYTIHWVKQRSGQGLEWIGWFYPGSGSI KYNEKFKDKATLTADKYSSTVYMELSSLTSED-SAVYFCARGGYYDSFDNWGQGTTLTV SS (SEQ ID NO: 10), wherein, CDR1 is GYTFTEYT (SEQ ID NO: 14),
CDR2 is FYPGSGSI (SEQ ID NO: 15), and
CDR3 is ARGGYYDSFDN (SEQ ID NO: 16).

In certain embodiments, this disclosure contemplates antibodies or antigen binding fragments comprising the heavy chain CDR3 and light chain CDR3 of AX2 antibodies. In certain embodiments, this disclosure contemplates antibodies or antigen binding fragments comprising the heavy chain CDR3 and light chain CDR3 of XII-24 antibodies.

In certain embodiments, this disclosure contemplates antibodies or fragments that comprise the light and/or heavy chain sequences or CDRs disclosed herein or variants thereof. In certain embodiments, the variants have greater than 50%, 60%, 70%, 80%, 90%, or 95% sequence identity or similarity to sequences disclosed herein which are still capable of specifically binding a the binding partner of interest. In certain embodiments, the variant sequences or CDRs have less than 10 or 15 amino acid substitutions. In certain embodiments, the variants have less than 2 or 3 substitutions, or have less than 4 or 5 substitutions, or have less than 6 or 7 substitutions. In certain embodiments, the variants have less than 2 or 3 conserved substitutions, or have less than 4 or 5 conserved substitutions, or have less than 6 or 7 conserved substitutions. In certain embodiments, the amino acid substitutions are not in the CDRs.

In certain embodiments, the CDR1 of the light chain has 1 or 2 substitutions. In certain embodiments, the CDR1 of the light chain has 3 or 4 substitutions. In certain embodiments, the CDR2 of the light chain has 1 or 2 substitutions. In certain embodiments, the CDR2 of the light chain has 3 or 4 substitutions. In certain embodiments, the CDR3 of the light chain has 1 or 2 substitutions. In certain embodiments, the CDR3 of the light chain has 3 or 4 substitutions.

In certain embodiments, the CDR1 of the heavy chain has 1 or 2 substitutions. In certain embodiments, the CDR1 of the heavy chain has 3 or 4 substitutions. In certain embodiments, the CDR2 of the heavy chain has 1 or 2 substitutions. In certain embodiments, the CDR2 of the heavy chain has 3 or 4 substitutions. In certain embodiments, the CDR3 of the heavy chain has 1 or 2 substitutions. In certain embodiments, the CDR3 of the heavy chain has 3 or 4 substitutions.

In certain embodiments, this disclosure contemplates using antibodies disclosed herein, e.g., XII-24 and AX2 antibodies, in immunological assays for detecting HCA in a sample. In certain embodiments, the disclosure relates to methods comprising: mixing a sample with an anti-idiotypic antibody that binds to anti-HCA antibodies providing a mixed sample; mixing the mixed sample with anti-HCA antibodies bound to a solid substrate providing immobilized anti-idiotypic antibodies and optionally immobilized HCA on the surface; labeling the anti-idiotypic antibodies; and quantitating the label on the surface. In certain embodiments, the anti-idiotypic antibodies are XII-24 antibodies, and the anti-HCA antibodies are AX2 antibodies.

In certain embodiments, this disclosure relates to methods of determining the presence of HCA in a sample comprising, providing a solid surface immobilized with an antibody that binds HCA, mixing a sample to be tested for the presence of HCA with an anti-idiotypic antibody that binds the variable regions on the surface immobilized antibody providing a test mixture; exposing the test mixture to the surface immobilized antibody under conditions such that an anti-idiotypic antibody in the sample is capable of binding surface immobilized antibody; and detecting a decrease of antibody and anti-idiotypic antibody binding indicting the presence of HCA in the sample.

In certain embodiments, this disclosure relates to kits for diagnosis of cancer. In one embodiment, the kit comprises an anti-idiotypic antibody or antigen-binding fragment thereof which binds to the variable region of an antibody that binds to HCA and suitable ancillary reagents. In certain embodiments, the kit further comprises an antibody that binds to HCA.

In certain embodiments, the kit comprises one or more of the following components: an anti-idiotypic antibody (XII-24) to the detecting antibody, anti-HCA antibody, (AX2); a suitable immobilized phase (e.g., micro titer plates, insoluble polymeric beads or particles) that can be washed and separated from a reaction mixture and are suitable for the immobilization of an antibody disclosed herein; a specific antibody (AX2 or AE3) with high affinity to HCA that can be detected using a detection method (e.g., radiation, colorimeteric, enzymatic, chemiluminecence, etc.), either directly or indirectly; a series of calibration material (calibrators) comprised of materials that emulate HCA in patient samples that can be used to establish an appropriate response curve to map detection signal into concentration of HCA; and any required blocking agents and buffers that inhibit nonspecific binding or any other signal generating reactions that are unrelated to HCA concentration.

BRIEF DESCRIPTION OF THE DRAWINGS

FIG. 3A shows the amino acid sequence of the light (K) chain (SEQ ID NO: 17) and nucleic acid sequence encoding the light (K) chain (SEQ ID NO: 18) for AX2.

FIG. 3B shows the amino acid sequence of the heavy chain (SEQ ID NO: 19) and the nucleic acid sequence encoding the heavy (SEQ ID NO: 20) chain for AX2.

FIG. 4A shows the amino acid sequence of the light (K) chain (SEQ ID NO: 21) and nucleic acid sequence encoding the light (K) chain (SEQ ID NO: 22) for XII-24.

FIG. 4B shows the amino acid sequence of the heavy chain (SEQ ID NO: 23) and the nucleic acid sequence encoding the heavy (SEQ ID NO: 24) chain for XII-24.

DETAILED DISCUSSION

Figure 1:
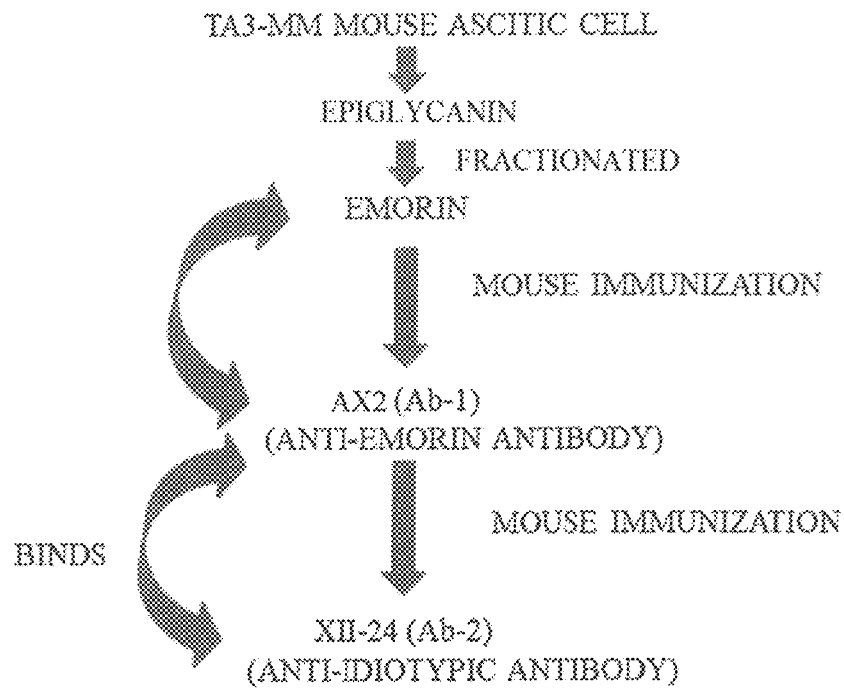
FIG. 1 illustrates the production and the binding properties of antibody AX2 and anti-idiotypic antibody XII-24. In the mouse, epiglycanin was found to be a mixture of highly glycosylated proteins (2-% protein by weight) of the mucin type, with a long extended protein chain to which are attached many short (2 to 7 carbohydrate residues) (carbohydrate 80% by weight). An epiglycanin type of strongly acidic properties (Emorin) was isolated both by size exclusion and affinity chromatography. Emorin was used for the immunization of C57BL mice to produce anti-Emorin lymphocytes. Using procedures for the production of monoclonal antibodies (i.e., immunization, fusion of lymphocytes with mouse myeloma cells to produce hybridoma cells, selection of the hybridoma cells that secreted antibodies with the desired specificity, growth of that hybridoma cell in culture), an anti-Emorin antibody with the desired properties, AX2, was produced.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

As used in this disclosure and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") have the meaning ascribed to them in U.S. patent law in that they are inclusive or open-ended and do not exclude additional, unrecited elements or method steps. The term "comprising" in reference to a peptide having an amino acid sequence refers to a peptide that may contain additional N-terminal (amine end) or C-terminal (carboxylic acid end) amino acids, i.e., the term is intended to include the amino acid sequence within a larger peptide. "Consisting essentially of" or "consists of" or the like, when applied to methods and compositions encompassed by the present disclosure refers to compositions like those disclosed herein that exclude certain prior art elements to provide an inventive feature of a claim, but which may contain additional composition components or method steps composition components or method steps, etc., that do not materially affect the basic and novel characteristic(s) of the compositions or methods, compared to those of the corresponding compositions or methods disclosed herein. The term "consisting of" in reference to a peptide having an amino acid sequence refers a peptide having the exact number of amino acids in the sequence and not more or having not more than a range of amino acids expressly specified in the claim.

As used herein, "subject" refers to any animal, preferably a human patient, livestock, or domestic pet.

As used herein a "sample" refers to a composition taken from or originating from a subject. Examples of samples include cell samples, blood samples, serum or plasma samples, tissue samples, hair samples, semen, and urine or excrement samples.

A "heterologous" nucleic acid or amino acid sequences refer to sequences that do not naturally occur together in a natural setting depending on the context, such as, in sequence identity or the relative location of the sequences in reference to each other. For example, when a heterologous peptide is conjugated or fused to an antibody, the peptide sequence does not occur in naturally occurring antibodies or, if the sequence does occur in antibodies, the sequence does not occur naturally in the specific location when produced in the living organism. In another example, animals have different nucleic acid sequences that are distinct in sequence from other plants, bacteria, viruses, or other organisms. Inserting a gene that expresses an animal protein into a viral based vector or plasmid is heterologous because the combination of animal and viral or plasmid sequences do not exist naturally. In the case where a nucleic acid encodes the same polypeptide sequence expressed in both organisms, the nucleic acid sequences are still not naturally occurring, as codons usage in different organisms are unique.

The terms "vector" or "expression vector" refer to a recombinant nucleic acid containing a desired coding sequence and appropriate nucleic acid sequences necessary for the expression of the operably linked coding sequence in a particular host organism or expression system, e.g., cellular or cell-free. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

Protein "expression systems" refer to in vivo and in vitro (cell free) systems. Systems for recombinant protein expression typically utilize cells transfecting with a DNA expression vector that contains the template. The cells are cultured under conditions such that they translate the desired protein. Expressed proteins are extracted for subsequent purification. In vivo protein expression systems using prokaryotic and eukaryotic cells are well known. Also, some proteins are recovered using denaturants and protein-refolding procedures. In vitro (cell-free) protein expression systems typically use translation-compatible extracts of whole cells or compositions that contain components sufficient for transcription, translation and optionally post-translational modifications such as RNA polymerase, regulatory protein factors, transcription factors, ribosomes, tRNA cofactors, amino acids and nucleotides. In the presence of an expression vectors, these extracts and components can synthesize proteins of interest. Cell-free systems typically do not contain proteases and enable labeling of the protein with modified amino acids. Some cell free systems incorporated encoded components for translation into the expression vector. See, e.g., Shimizu et al., Cell-free translation reconstituted with purified components, 2001, Nat. Biotechnol., 19, 751-755 and Asahara & Chong, Nucleic Acids Research, 2010, 38(13): e141, both hereby incorporated by reference in their entirety.

A "selectable marker" is a nucleic acid introduced into a recombinant vector that encodes a polypeptide that confers a trait suitable for artificial selection or identification (report gene), e.g., beta-lactamase confers antibiotic resistance, which allows an organism expressing beta-lactamase to survive in the presence antibiotic in a growth medium. Another example is thymidine kinase, which makes the host sensitive to ganciclovir selection. It may be a screenable marker that allows one to distinguish between wanted and unwanted cells based on the presence or absence of an expected color. For example, the lac-z-gene produces a beta-galactosidase enzyme which confers a blue color in the presence of X-gal (5-bromo-4-chloro-3-indolyl-β-D-galactoside). If recombinant insertion inactivates the lac-z-gene, then the resulting colonies are colorless. There may be one or more selectable markers, e.g., an enzyme that can complement to the inability of an expression organism to synthesize a particular compound required for its growth (auxotrophic) and one able to convert a compound to another that is toxic for growth. URA3, an orotidine-5' phosphate decarboxylase, is necessary for uracil biosynthesis and can complement ura3 mutants that are auxotrophic for uracil. URA3 also converts 5-fluoroorotic acid into the toxic compound 5-fluorouracil. Additional contemplated selectable markers include any genes that impart antibacterial resistance or express a fluorescent protein. Examples include, but are not limited to, the following genes: ampr, camr, tetr, blasticidinr, neor, hygr, abxr, neomycin phosphotransferase type II gene (nptII), p-glucuronidase (gus), green fluorescent protein (gfp), egfp, yfp, mCherry, p-galactosidase (lacZ), lacZa, lacZAM15, chloramphenicol acetyltransferase (cat), alkaline phosphatase (phoA), bacterial luciferase (luxAB), bialaphos resistance gene (bar), phosphomannose isomerase (pmi), xylose isomerase (xylA), arabitol dehydrogenase (atlD), UDP-glucose:galactose-1-phosphate uridyltransferasel (galT), feedback-insensitive α subunit of anthranilate synthase (OASA1D), 2-deoxyglucose (2-DOGR), benzyladenine-N-3-glucuronide, *E. coli* threonine deaminase, glutamate 1-semialdehyde aminotransferase (GSA-AT), D-amino acidoxidase (DAAO), salt-tolerance gene (rstB), ferredoxin-like protein (pflp), trehalose-6-P synthase gene (AtTPS1), lysine racemase (lyr), dihydrodipicolinate synthase (dapA), tryptophan synthase beta 1 (AtTSB1), dehalogenase (dhlA), mannose-6-phosphate reductase gene (M6PR), hygromycin phosphotransferase (HPT), and D-serine ammonialyase (dsdA).

A "label" refers to a detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "label receptor" refers to incorporation of a heterologous polypeptide in the receptor. A label includes the incorporation of a radiolabeled amino acid or the covalent attachment of biotinyl moieties to a polypeptide that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}S$ or $^{131}I$) fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

In certain embodiments, the disclosure relates to antibodies and antigen binding fragments comprising sequences disclosed herein or variants or fusions thereof wherein the amino terminal end or the carbon terminal end of the amino acid sequence are optionally attached to a heterologous amino acid sequence, label, or reporter molecule.

In certain embodiments, the disclosure relates to vectors comprising a nucleic acid encoding an antibody or antigen binding fragment disclosed herein or chimeric protein thereof.

In certain embodiments, the vector optionally comprises a mammalian, human, insect, viral, bacterial, bacterial plasmid, yeast associated origin of replication or gene such as a gene or retroviral gene or lentiviral LTR, TAR, RRE, PE, SLIP, CRS, and INS nucleotide segment or gene selected from tat, rev, nef, vif, vpr, vpu, and vpx or structural genes selected from gag, pol, and env.

In certain embodiments, the vector optionally comprises a gene vector element (nucleic acid) such as a selectable marker region, lac operon, a CMV promoter, a hybrid chicken B-actin/CMV enhancer (CAG) promoter, tac promoter, T7 RNA polymerase promoter, SP6 RNA polymerase promoter, SV40 promoter, internal ribosome entry site (IRES) sequence, cis-acting woodchuck post regulatory regulatory element (WPRE), scaffold-attachment region (SAR), inverted terminal repeats (ITR), FLAG tag coding region, c-myc tag coding region, metal affinity tag coding region, streptavidin binding peptide tag coding region, polyHis tag coding region, HA tag coding region, MBP tag coding region, GST tag coding region, polyadenylation coding region, SV40 polyadenylation signal, SV40 origin of replication, Col E1 origin of replication, f1 origin, pBR322 origin, or pUC origin, TEV protease recognition site, loxP site, Cre recombinase coding region, or a multiple cloning site such as having 5, 6, or 7 or more restriction sites within a continuous segment of less than 50 or 60 nucleotides or having 3 or 4 or more restriction sites with a continuous segment of less than 20 or 30 nucleotides.

In certain embodiments, term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity.

In certain embodiments, sequence "identity" refers to the number of exactly matching amino acids (expressed as a percentage) in a sequence alignment between two sequences of the alignment calculated using the number of identical positions divided by the greater of the shortest sequence or the number of equivalent positions excluding overhangs wherein internal gaps are counted as an equivalent position. In certain embodiments, any recitation of sequence identity expressed herein may be substituted for sequence similarity. Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic—F Y W; hydrophobic—A V I L; Charged positive: R K H; Charged negative—D E; Polar—S T N Q.

This disclosure contemplates "conservative sequence modifications" of the sequences disclosed herein, including nucleotide and amino acid sequence modifications which do not significantly affect or alter the binding characteristics of the antibody encoded by the nucleotide sequence or containing the amino acid sequence. Such conservative sequence modifications include nucleotide and amino acid substitutions, additions and deletions. Modifications can be introduced into the sequences disclosed herein by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

Antibodies

In certain embodiments, this disclosure relates to antibodies that bind human carcinoma antigen (HCA). In certain embodiments, this disclosure relates to anti-idiotypic antibodies or fragments that bind the variable regions of antibodies that bind HCA. In certain embodiments, the antibodies that bind HCA are derived from the AX2 antibody or fragments. In certain embodiments the anti-idiotypic antibodies are derived from the XII-24 antibody or fragments.

In certain embodiments, the CDRs comprise the light chain XII-24 variable region CDRs within DILMTQSPSSMSVSLGDTVSITCHASQGIS-GNIGWLQQKPGKSFKGLIYHGTNLEDGVPS RFSGSGSGADYSLTISSLESED-FADYYCVQYIQFPFTFGGGTKLEIKR (SEQ ID NO: 1), wherein, CDR1 is QGISGN (SEQ ID NO: 3), CDR2 is HGTN (SEQ ID NO: 4), and CDR3 is VQYIQFPFT (SEQ ID NO: 5); and the three heavy chain XII-24 variable region CDRs within QVHLKQSGAEVVRPGASLKLSCK-ASGYIFTDYYVHWAKQRPGQGLEWIARIYPGSGNT YYNEKFMVKATLTAESSSSTAYMELSRLTSED-SAVYFCASSLYYPLDHWGQGTSVIVSS (SEQ ID NO: 2), wherein, CDR1 is GYIFTDYY (SEQ ID NO: 6), CDR2 is IYPGSGNT (SEQ ID NO: 7), and CDR3 is ASSLYYPLDH (SEQ ID NO: 8).

In certain embodiments, the CDRs comprise the light chain AX2 variable region CDRs within GIVMTQSHKFMSTSIGDRVSITCKASQDVGTA-VAWYQQKPGQSPKLLIFWASTRHTGVP DRFTGSGSGTDFTLTISNVQSEDLADYFCQHYINY-PLTFGAGTKLELK (SEQ ID NO: 9), wherein, CDR1 is QDVGTA (SEQ ID NO: 11), CDR2 is WAST (SEQ ID NO: 12), and CDR3 is QHYINYPLT (SEQ ID NO: 13); and the three heavy chain AX2 variable region CDRs within QVQLQQSGAELVKPGASVKLSCK-ASGYTFTEYTIHWVKQRSGQGLEWIGWFYPGSGSI KYNEKFKDKATLTADKYSSTVYMELSSLTSED-SAVYFCARGGYYDSFDNWGQGTTLTV SS (SEQ ID NO: 10), wherein, CDR1 is GYTFTEYT (SEQ ID NO: 14), CDR2 is FYPGSGSI (SEQ ID NO: 15), and CDR3 is ARGGYYDSFDN (SEQ ID NO: 16).

In certain embodiments, the antibodies disclosed herein are conjugated to a label, fluorescent dye, quantum dot, nanoparticle, heterologous polypeptide, an enzyme, or solid surface. In certain embodiments, the antibody is a chimeric antibody or humanized antibody.

In certain embodiments, this disclosure relates to hybridoma that produces the antibodies disclosed herein.

In certain embodiments, the disclosure relates to vectors comprising a nucleic acid sequence encoding the light chain and/or the heavy chain of an antibody disclosed herein.

In certain embodiments, the vector comprises a heterologous nucleic acid sequence or heterologous promoter or encodes a selectable marker.

In certain embodiments, this disclosure relates to expression system comprising a vector disclosed herein. In certain embodiments, the expression system is a cell.

As used herein, the term "antibody" is intended to denote an immunoglobulin molecule that possesses a "variable region" antigen recognition site. The term "variable region" is intended to distinguish such domain of the immunoglobulin from domains that are broadly shared by antibodies (such as an antibody Fc domain). The variable region comprises a "hypervariable region" whose residues are responsible for antigen binding. The hypervariable region comprises amino acid residues from a "Complementarity Determining Region" or "CDR" (i.e., typically at approximately residues 24-34 (L1), 50-56 (L2) and 89-97 (L3) in the light chain variable domain and at approximately residues 27-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, J. Mol. Biol. 196:901-917). "Framework Region" or "FR" residues are those variable domain residues other than the hypervariable region residues as herein defined. The term antibody includes monoclonal antibodies, multi-specific antibodies, human antibodies, humanized antibodies, synthetic antibodies, chimeric antibodies, camelized antibodies (See e.g., Muyldermans et al., 2001, Trends Biochem. Sci. 26:230; Nuttall et al., 2000, Cur. Pharm. Biotech. 1:253; Reichmann and Muyldermans, 1999, J. Immunol. Meth. 231:25; International Publication Nos. WO 94/04678 and WO 94/25591; U.S. Pat. No. 6,005,079), single-chain Fvs (scFv) (see, e.g., see Pluckthun in The Pharmacology of Monoclonal Antibodies, vol. 113, Rosenburg and Moore eds. Springer-Verlag, New York, pp. 269-315 (1994)), single chain antibodies, disulfide-linked Fvs (sdFv), intrabodies, and anti-idiotypic (anti-Id) antibodies (including, e.g., anti-Id and anti-anti-Id antibodies to the disclosed B7-H5 antibodies). In particular, such antibodies include immunoglobulin molecules of any type (e.g., IgG, IgE, IgM, IgD, IgA and IgY), class (e.g., IgG1, IgG2, IgG3, IgG4, IgA1 and IgA2) or subclass.

In certain embodiments, antibodies disclosed herein, fragment, or heavy chain comprise a variant Fc domain. As used herein a "variant Fc domain" refers to an Fc domain engineered to comprise at least one amino acid modification relative to a wild-type Fc domain.

As used herein, a molecule is said to be able to "immunospecifically bind" a second molecule if such binding exhibits the specificity and affinity of an antibody to its cognate antigen. Antibodies are said to be capable of "immunospecifically binding" to a target region or conformation ("epitope") of an antigen if such binding involves the antigen recognition site of the immunoglobulin molecule. An antibody that immunospecifically binds to a particular antigen may bind to other antigens with lower affinity if the other antigen has some sequence or conformational similarity that is recognized by the antigen recognition site as determined by, e.g., immunoassays, but would not bind to a totally unrelated antigen. Preferably, however, antibodies (and their antigen binding fragments) will not cross-react with other antigens. Antibodies may also bind to other molecules in a way that is not immunospecific, such as to FcR receptors, by virtue of binding domains in other regions/domains of the molecule that do not involve the antigen recognition site, such as the Fc region.

As used herein, the term "antigen binding fragment" of an antibody refers to one or more portions of an antibody that contain the antibody's Complementarity Determining Regions ("CDRs") and optionally the framework residues that comprise the antibody's "variable region" antigen recognition site, and exhibit an ability to immunospecifically bind an antigen. Such fragments include Fab', F(ab')2, Fv, single chain (ScFv), and mutants thereof, naturally occurring variants, and fusion proteins comprising the antibody's "variable region" antigen recognition site and a heterologous protein (e.g., a toxin, an antigen recognition site for a different antigen, an enzyme, a receptor or receptor ligand, etc.). As used herein, the term "fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

Human, non-naturally occurring chimeric or humanized derivatives of antibodies are particularly preferred for in vivo use in humans, however, murine antibodies or antibodies of other species may be advantageously employed for many uses (for example, in vitro or in situ detection assays, acute in vivo use, etc.). A humanized antibody may comprise amino acid residue substitutions, deletions or additions in one or more non-human CDRs. The humanized antibody derivative may have substantially the same binding, stronger binding or weaker binding when compared to a non-derivative humanized antibody. In specific embodiments, one, two, three, four, or five amino acid residues of the CDR have been substituted, deleted or added (i.e., mutated). Completely human antibodies are particularly desirable for therapeutic treatment of human subjects.

Human antibodies can be made by a variety of methods known in the art including phage display methods described above using antibody libraries derived from human immunoglobulin sequences (see U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741). Human antibodies can be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized using conventional methodologies with a selected antigen, e.g., all or a portion of a polypeptide.

Monoclonal antibodies directed against the antigen can be obtained from the immunized, transgenic mice using conventional hybridoma technology (see, e.g., U.S. Pat. No. 5,916,771). The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93, which is incorporated herein by reference in its entirety). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies such as Abgenix, Inc. (Freemont, Calif.) and Medarex (Princeton, N.J.) can be engaged to provide human antibodies directed against a selected antigen using technology similar to that described above.

A "chimeric antibody" is a molecule in which different portions of the antibody are derived from different immunoglobulin molecules such that the entire molecule is not naturally occurring. Examples of chimeric antibodies include those having a variable region derived from a non-human antibody and a human immunoglobulin constant region such as antibodies that have murine variable domains and human constant domains. Chimeric antibodies include humanized antibodies, i.e., antibodies having murine CDRs but are otherwise human. The term is also intended to include antibodies having a variable region derived from one human antibody grafted to an immunoglobulin constant region of a predetermined sequences or the constant region from another human for which there are allotypic differences residing in the constant regions of any naturally occurring antibody having the variable regions, e.g., CDRs 1, 2, and 3 of the light and heavy chain. Human heavy chain genes exhibit structural polymorphism (allotypes) that are inherited as a haplotype. The serologically defined allotypes differ within and between population groups. See Jefferis et al. mAb, 1 (2009), pp. 332-338.

Smith et al. report a protocol for the production of antigen-specific chimeric human monoclonal antibodies (hmAbs) wherein antibody-secreting cells (ASCs) are isolated from whole blood collected after vaccination and sorted by flow cytometry into single cell plates. Nat Protoc. 2009, 4(3):372-84. The antibody genes of the ASCs are then amplified by RT-PCR and nested PCR, cloned into expression vectors and transfected into a human cell line. Meijer et al. report methods for isolation of human antibody repertoires with preservation of the natural heavy and light chain pairing. J Mol Biol. 2006, 358(3):764-72. Wrammert et al. report using immunoglobulin variable regions isolated from sorted single ASCs to produce human monoclonal antibodies (mAbs) that bound with high affinity. Nature. 2008, 453(7195): 667-671.

Methods for producing chimeric antibodies are known in the art. See e.g., Morrison, 1985, Science 229:1202; Oi et al., 1986, BioTechniques 4:214; Gillies et al., 1989, J. Immunol. Methods 125:191-202; and U.S. Pat. Nos. 6,311,415, 5,807,715, 4,816,567, and 4,816,397. Chimeric antibodies comprising one or more CDRs from a non-human species and framework regions from a human immunoglobulin molecule can be produced using a variety of techniques known in the art including, for example, CDR-grafting (EP 239,400; International Publication No. WO 91/09967; and U.S. Pat. Nos. 5,225,539, 5,530,101, and 5,585,089), veneering or resurfacing (EP 592,106; EP 519,596; Padlan, 1991, Molecular Immunology 28(4/5):489-498; Studnicka et al., 1994, Protein Engineering 7:805; and Roguska et al., 1994, Proc. Natl. Acad. Sci. USA 91:969), and chain shuffling (U.S. Pat. No. 5,565,332).

As used herein, the term "humanized antibody" refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor." Constant regions need not be present, but if they are, they must be substantially identical to human immunoglobulin constant regions, i.e., at least about 85-90%, preferably about 95% or more identical. Hence, all parts of a humanized immunoglobulin, except possibly the CDR's, are substantially identical to corresponding parts of natural human immunoglobulin sequences. A humanized antibody is an antibody comprising a humanized light chain and a humanized heavy chain immunoglobulin. For example, a humanized antibody would not encompass a typical chimeric antibody, because, e.g., the entire variable region of a chimeric antibody is non-human. One says that the donor antibody has been "humanized," by the process of "humanization," because the resultant humanized antibody is expected to bind to the same antigen as the donor antibody that provides the CDR's. For the most part, humanized antibodies are human immunoglobulins (recipient antibody) in which hypervariable region residues of the recipient are replaced by hypervariable region residues from a non-human species (donor antibody) such as mouse, rat, rabbit or a non-human primate having the desired specificity, affinity, and capacity. In some instances, Framework Region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin that immunospecifically binds to an Fc RIIB polypeptide, that has been altered by the introduction of amino acid residue substitutions, deletions or additions (i.e., mutations).

DNA sequences coding for preferred human acceptor framework sequences include but are not limited to FR segments from the human germline VH segment VH1-18 and JH6 and the human germline VL segment VK-A26 and JK4. In a specific embodiment, one or more of the CDRs are inserted within framework regions using routine recombinant DNA techniques. The framework regions may be naturally occurring or consensus framework regions, and preferably human framework regions (see, e.g., Chothia et al., 1998, "Structural Determinants In the Sequences of Immunoglobulin Variable Domain," J. Mol. Biol. 278: 457-479 for a listing of human framework regions).

In certain embodiments, this disclosure relates to antibodies or antigen binding fragments comprising six complementary determining regions (CDRs) or consensus sequences thereof, wherein the CDRs comprise the three heavy and/or light chain CDRs of the antibody derived from the XII-24 or AX2. In certain embodiments, antibodies or antigen binding fragments bind the variable regions of antibodies derived from the AX2 hybridoma. In certain embodiments, the disclosure contemplates that any of the antibody sequences disclosed herein may be changed or contain at least one non-naturally occurring substitution modification relative to wild-type sequences or the sequence reported.

Antibodies to HCA and methods for their production have been described in U.S. Pat. Nos. 5,808,005; 5,693,763; 5,545,532. Antibodies to epiglycanin and methods for their production have also been described in the art. For example, monoclonal antibodies to epiglycanin and methods for their production are described, for example, in U.S. Pat. Nos. 4,837,171, 5,545,532, and Haavik et al., Glycobiology, 2:217-224 (1992). Hybridomas producing anti-murine epiglycanin antibodies, AE-1, AE-3 and AE-4, have been deposited with the American Type Culture Collection (ATCC), P.O. Box 1549, Manassas, Va. 20108 USA. For example, the hybridoma HAE-1 (producing monoclonal antibody AE-1) was deposited at the ATCC under accession no. HB-9466. The hybridoma HAE-3 (producing monoclonal antibody AE-3) was deposited at the ATCC under accession no. HB-9467. The hybridoma HAE-4 (producing monoclonal antibody AE-4) was deposited at the ATCC under accession no. HB-9468. Monoclonal antibody AE-3 cross-reacts and binds with HCA.

In practice, a monoclonal antibody is an antibody derived from a single hybridoma cell, after cloning. Thus, all hybridoma cells from a particular hybridoma cell inherit the same specificity. They are monoclonal. A good example is the experiment that produced that produced the AE-1, AE-3, and AE-4 monoclonal antibodies. These were all produced after immunization with the heterogeneous, but structurally-related, mixture of glycoproteins, which is epiglycanin. Epiglycanin contains many epitopes, each capable of producing a lymphocyte of a specific activity. After fusion of the lymphocytes with mouse myeloma (cancer) cells, to form hybridoma cells, each now having a single specificity (from a single myeloma cell), the mixture was cloned, and a new culture, each with a single specificity was established from each successful hybridoma cell (each culture produces a new monoclonal antibody). Each of the three monoclonal antibodies resulting from that experiment (AE-1, AE-3, and AE-4) possesses a different specificity. The AX2 antibody, which was recently produced in a separate experiment, resulted from the immunization of a C57BL mouse with a purified epiglycanin, Emorin, a glycoprotein component of the epiglycanin mixture. The resulting antibody, AX2, has good stability and strong binding activity for HCA.

Antibodies can be polyclonal or monoclonal, and the term "antibody" is intended to encompass both polyclonal and monoclonal antibodies. The terms polyclonal and monoclonal refer to the degree of homogeneity of an antibody preparation, and are not intended to be limited to particular methods of production. The term "antibody", as used herein, also encompasses functional fragments of antibodies, including fragments of human, chimeric, humanized, primatized, veneered or single chain antibodies. Functional fragments include antigen-binding fragments specific for HCA. Antigen-binding fragments specific for HCA include, but are not limited to, Fab, Fab', $F(ab')_2$ and Fv fragments. Such fragments can be produced by enzymatic cleavage or recombinant techniques. For example, papain or pepsin cleavage can generate Fab or $F(ab')_2$ fragments, respectively. Other proteases with the requisite substrate specificity can also be used to generate Fab or $F(ab')_2$ fragments. Antibodies can also be produced in a variety of truncated forms using antibody genes in which one or more stop codons has been introduced upstream of the natural stop site. For example, a chimeric gene encoding a $F(ab')_2$ heavy chain portion can be designed to include DNA sequences encoding the $CH_1$ domain and hinge region of the heavy chain.

Single chain antibodies, and chimeric, humanized or primatized (CDR-grafted), or veneered antibodies, as well as chimeric, CDR-grafted or veneered single chain antibodies, comprising portions derived from different species, and the like are also contemplated by the present disclosure. The various portions of antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0 125 023 B1; Boss et al., U.S. Pat. No. 4,816,397; Boss et al., European Patent No. 0 120 694 B1; Neuberger et al., International Publication No. WO86/01533; Neuberger et al., European Patent No. 0 194 276 B1; issued to Winter et al., U.S. Pat. No. 5,225,539; issued to Winter et al., European Patent No. 0 239 400 B1; Queen et al., European Patent No. 0 451 216 B1; and Padlan et al., EP 0 519 596 A1. See also, Newman et al., BioTechnology, 10: 1455-1460 (1992), regarding primatized antibody, and Ladner et al., U.S. Pat. No. 4,946,778 and Bird et al., Science, 242:423-426 (1988)) regarding single chain antibodies.

An “antigen” is a molecule or a portion of a molecule capable of being bound by an antibody which is additionally capable of inducing an animal to produce antibody capable of binding to an epitope of that antigen. An antigen can have one or more than one epitope.

The term “epitope” is meant to refer to that portion of the antigen capable of being recognized by and bound by an antibody at one or more of the antibody’s antigen binding region. Epitopes usually consist of chemically active surface groupings of molecules such as amino acids or sugar side chains and have specific three dimensional structural characteristics as well as specific charge characteristics.

Immunological Assays for Detecting HCA in a Sample

It has been discovered that HCA, as well as its counterpart in the mouse, i.e., the active component of the epiglycanin mixture of mucin-type glycoproteins reported herein as Emorin, exists in the blood of subjects not as free glycoproteins but as their antibody complexes. This disclosure relates to antibodies (AX2 and XII-24) used in the detection of the Human Carcinoma Antigen (HCA) (in humans) and Emorin (in the mouse), both found as antibody complexes in body fluids. The detection of the complex, performed by the DOC (Detection of Carcinoma) Assay provides a highly sensitive method for the determination of the presence of a carcinoma in humans.

Disclosed herein is a clinical test for cancer present in epithelial tissue (i.e., carcinomas). This includes many common cancers, such as breast, prostate, lung, kidney and colon, as well as those more difficult to detect, such as pancreas and ovarian cancer. A carcinoma is indicated by the presence of the Human Carcinoma Antigen (HCA)-anti-HCA in the blood (HCA-anti-HCA complex).

The test involves a competition for the HCA between one of the monoclonal antibodies coating the plate (AX2) and the other monoclonal antibody (XII-24) in solution with the sample, e.g., serum, being tested. The results are recorded as the percent of the amount of HCA in the serum relative to the amount in a positive or negative control. The assay is capable of distinguishing between carcinoma patients and normal persons with high accuracy.

Methods disclosed herein for the detection of HCA use a sample. In certain embodiments, sample materials may include bodily fluids including plasma, serum, whole blood, spinal fluid, semen, vaginal fluids, sputum and saliva, cerebrospinal fluid, lymphatic fluid and digestive fluids. Other sample materials may include isolated or enriched cell populations and tissues. Samples may be fresh or fixed (preserved). Fixed samples may be embedded (for example, paraffin embedded).

In certain embodiments, this disclosure contemplates using antibodies disclosed herein, e.g., XII-24 and AX2 antibodies, in immunological assays for detecting HCA in a sample. In certain embodiments, this disclosure relates to methods of determining the presence of HCA in a sample comprising, providing a solid surface immobilized with an antibody that binds HCA, mixing a sample to be tested for the presence of HCA with an anti-idiotypic antibody that binds the variable regions on the surface immobilized antibody providing a test mixture; exposing the test mixture to the surface immobilized antibody under conditions such that anti-idiotypic antibody in the sample is capable of binding surface immobilized antibody; and detecting a decrease of antibody and anti-idiotypic antibody binding, indicting the presence of HCA in the sample.

In certain embodiments, this disclosure relates to methods of determining the presence of antigen in a sample, wherein the antigen is suspected to contain autoantibodies comprising, mixing a sample to be tested for the presence of antigen having autoantibodies with an anti-idiotypic antibody that binds the variable regions on the autoantibodies providing a test mixture that liberates the antigen; exposing the test mixture anti-antigen antibodies; and detecting the binding of anti-antigen antibodies to the antigen.

In certain embodiments, this disclosure relates to uses of antibodies disclosed herein in an immunological assays to detect HCA. In certain embodiments, this disclosure relates to methods comprising mixing an anti-idiotypic antibody disclosed herein with antibody that binds HCA or epiglycanin under conditions such that the anti-idiotypic antibody binds to the variable region of the antibody that binds HCA or epiglycanin.

In certain embodiments, this disclosure relates to methods for diagnosis of cancer in a human subject comprising determining the level of HCA in a sample from the subject; and comparing the level determined to the level of HCA in a control sample.

Typically, a control sample is one supplied with the kit, such as a serum sample selected from a panel of sera from healthy persons who consistently give 0.0 percent inhibition in the DOC Assay. The level of HCA in a subject’s serum is defined as Percent Inhibition.

% Inhibition=Absorbance at 405 nm of:
Control Serum minus Subject Serum
Divided by: Control Serum×100

$$(\text{Control Serum}-\text{Subject Serum})/(\text{Control Serum})\times 100$$

In certain embodiments, this disclosure relates to methods for the diagnosis of cancer (carcinomas) in a human subject comprising contacting a sample (serum) from the subject with an antibody, (see FIG. 2), which will also cleave the HCA-anti-HCA complex.

Serum of free HCA has been found in the human (or a counterpart, such as Emorin, in the mouse). Thus, the DOC Assay, as described herein, determines the level of HCA in the HCA-anti-HCA antibody (HCA-anti-HCA) complex in carcinoma patients. In certain embodiments the presence of the HCA-anti-HCA in the serum of a subject (if the subject is affected with a carcinoma), may be detected for the HCA by incubating the sample with the anti-idiotypic antibody (XII-24), (or under different circumstances, with the anti-Emorin antibody AX2) (see FIG. 2) by cleaving the HCA-anti-HCA complex. The liberated HCA is then contacted by the XII-24 antibody to bind at the Fc region of the XII-24 antibody, leaving its hypervariable region free to bind to the hypervariable region of the AX2 antibody coating the surface of the plate. For the control serum, wherein there is no HCA complex, and, therefore there is no lost XII-24, the percent inhibition would be 0%. The difference in absorbance at 405 nm between the subject serum and the control serum, as expressed in percent terms, is a measure of the HCA present, any value above 0% inhibition is indicative of a carcinoma.

Immunoassays are any assays that can detect the binding (or absence of binding) of an antigen to an antibody or antigen-binding fragment and quantitate the presence of the antigen in the sample. Examples of suitable immunoassays include sandwich assays, radioimmunoassays and, preferably, competitive inhibition assays. The use of the term “antigen” or “inhibitor” in the context of a reagent in the assay is intended to include HCA, as well as functional variants and portions of HCA. An inhibitor, as used herein, refers to an antigen that is immunologically cross-reactive with HCA.

Generally, fragments or portions of HCA include those having a deletion (i.e., one or more deletions) of an amino acid (i.e., one or more amino acids) relative to the native (wildtype) HCA, respectively (such as N-terminal, C-terminal or internal deletions). Fragments or portions in which only contiguous amino acids have been deleted or in which non-contiguous amino acids have been deleted relative to native (wildtype) HCA are also envisioned.

In a radioimmunoassay (MA), the amount of antigen present in a sample is measured indirectly employing a limited amount of antibody (or antigen-binding fragment) to compete for labeled antigen. In an IRMA (immunoradiometric assay), antigen is assayed directly by reacting the antigen with excess labeled antibody (or antigen-binding fragment).

In one class of IRMA assays, the unknown antigen is insolubilized and reacted with labeled antibody (or antigen-binding fragment). When the antigen is insolubilized by reaction with solid-phase antibody (or antigen-binding fragment), the assay is termed a “two-site IRMA”, “junction test”, or “sandwich assay”. Sandwich assays are further classified according to their methodology as forward, reverse or simultaneous sandwich assays.

In a forward sandwich immunoassay, a sample containing the antigen can be first incubated with a solid-phase immunoadsorbent containing immobilized antibody (or antigen-binding fragment). Incubation is continued for a sufficient period of time to allow antigen in the sample to bind to immobilized antibody (or antigen-binding fragment) on the solid-phase immunoadsorbent. The solid-phase immunoadsorbent can then be separated from the incubation mixture and washed to remove excess antigen and other substances which also may be present in the sample. The solid-phase immunoadsorbent containing antigen (if any) bound to immobilized antibody (or antigen-binding fragment) can be subsequently incubated with labeled antibody (or antigen-binding fragment) capable of binding to the antigen. After the second incubation, another wash is performed to remove unbound labeled antibody (or antigen-binding fragment) from the solid-phase immunoadsorbent thereby removing non-specifically bound labeled antibody (or antigen-binding fragment). Labeled antibody (or antigen-binding fragment) bound to the solid-phase immunoadsorbent is then detected and the amount of labeled antibody (or antigen-binding fragment) detected can serve as a direct measure of the amount of antigen present in the sample. Such forward sandwich assays are described in the patent literature, and in particular, in U.S. Pat. Nos. 3,867,517 and 4,012,294, issued to Chung-Mei Ling, which are incorporated herein by reference.

In a reverse sandwich assay, a sample can be incubated with labeled antibody (or antigen-binding fragment) after which the solid-phase immunoadsorbent containing immobilized antibody (or antigen-binding fragment) is added and incubated. A washing step can be performed after the second incubation period. A reverse sandwich assay has been described in the patent literature in U.S. Pat. No. 4,098,876, issued to Roger N. Piasio et al.

In a simultaneous sandwich assay, a sample can be incubated simultaneously in one-step with both an immunoadsorbent containing immobilized antibody (or antigen-binding fragment) for the antigen and labeled antibody (or antigen-binding fragment) for the antigen. Thereafter, labeled antibody (or antigen-binding fragment) bound to the immunoadsorbent can be detected as an indication of the amount of antigen present in the sample. A simultaneous sandwich assay has been described in the patent literature in U.S. Pat. No. 4,837,167, issued to Hubert J. P. Schoemaker et al.

Many solid-phase immunoadsorbents can be employed. Well-known immunoadsorbents include beads formed from glass polystyrene, polypropylene, dextran, and other materials. Preferably, the solid support is a plate, stick, tube or foam or coated with such materials; etc. The antibody (or antigen-binding fragment) can be either covalently or physically bound to the solid-phase immunoadsorbent by techniques such as covalent bonding via an amide or ester linkage or adsorption.

A competitive inhibition immunoassay can be employed to determine the presence of an antigen in a sample by measuring the inhibition of formation of a competitive inhibitor-antibody (or competitive inhibitor-antigen-binding fragment) complex, one of which is typically bound and the other of which is typically labeled, by free antigen in the sample. In addition, a typical quantitative immunoassay kit can include a standardized sample of pure inhibitor, such as an antigen, so that a reference solution can be run together with the sample to minimize sampling errors and to assure precision.

Competitive immunoassays (e.g., radioimmunoassay (MA), enzyme-linked immunoadsorbant assay (ELISA)) are used to detect and quantitate the presence of antigen in a sample by determining the extent of inhibition by the antigen of a competitive inhibitor/antibody (or competitive inhibitor/antigen-binding fragment) reaction. Typically, either the inhibitor or the antibody (or antigen-binding fragment) is bound to a solid support (as described above), while the other component of the pair is labeled in some fashion to render it detectable. Methods that are used to detect and quantitate the presence of antigen in a sample are also referred to as serologic diagnostic methods.

Labels include, e.g., radionuclides (e.g., Florine-18, Tc-99m, Iodine-125, Iodine-131, Indium-111, Bismuth-210), enzymes which produce an absorptive or fluorescent detector group when reacted with a specific substrate (e.g., horseradish peroxidase, N-methylumbelliferone-o-D-galactosidase), dyes (chromophores), fluorescent compounds (e.g., fluorescein, rhodamine, phycoerythrin, cyamine dyes, other compound emitting fluorescence energy), electron dense compounds (e.g., gold and ferric chloride compounds). Biotin/avidin labeling systems can also be used. Coupled assays can also be used for detecting labels.

The label may be directly linked to the component (the inhibitor or antibody) or may be bound to it indirectly, e.g., by attaching the label to another molecule capable of recognizing a component of the antigen/antibody pair. For example, an antibody (or antigen-binding fragment) can be indirectly labeled by attaching an enzyme, fluorescent marker or radionuclide to an isotype-specific antibody which recognizes the non-variable region of the antigen-specific antibody (or antigen-binding fragment). In another embodiment, the label can be attached to an antibody (or antigen-binding fragment) which recognizes an available epitope of the antigen after it has been bound to the specific antibody (or antigen-binding fragment).

In one embodiment, the label is a dye (such as, nitrophenyl) attached to the unbound component or reagent (unbound inhibitor or antibody) via a phosphate linker. After incubation of the labeled component with the immobilized binding partner, the presence of binding can then be determined by subjecting the solid support to a phosphatase enzyme, causing hydrolysis of the dye. The presence (and amount) of the dye can then be measured by absorbance, indicating the amount of binding of the two components.

In each assay, the sample, antibody (or antigen-binding fragment) and, optionally, the inhibitor is incubated under conditions and for a period of time sufficient to allow antigen to bind to the antibody (or antigen-binding fragment), i.e., under conditions suitable for the formation of a complex between the antigen and antibody (or antigen-binding fragment). In general, it is usually desirable to provide incubation conditions sufficient to bind as much antigen or inhibitor as possible because this maximizes the binding of labeled antibody or antigen-binding fragment) to the antigen thereby increasing the signal. Suitable temperatures are generally below the temperature at which denaturation can occur.

The presence of an increased (elevated) level of HCA reactivity (found as complex with its antibody) in a sample obtained from a subject can be indicative of malignancy associated with cancer. Measurement of HCA in a sample can provide early diagnosis of prostate cancer and the opportunity for early treatment.

Suitable antibodies, and antigen-binding fragments thereof, for use in determining the presence of HCA bind to the antigen HCA. Such antibodies include antibodies to HCA, as well as antibodies to epiglycanin that cross-react and bind HCA.

Kits

Kits for use in detecting the presence of HCA in a sample can also be prepared. Such kits can include an antibody, anti-idiotypic antibody, or antigen-binding fragment disclosed herein, as well as one or more ancillary reagents. The antibody or antigen binding fragment compositions can be provided in lyophilized form, either alone or in combination with additional antibodies specific for other epitopes. The antibodies or antigen-binding fragments, which can be labeled or unlabeled, can be included in the kits with adjunct ingredients (e.g., buffers, such as Tris, phosphate and carbonate, stabilizers, excipients, biocides and/or inert proteins, e.g., bovine serum albumin). For example, the antibodies or antigen-binding fragments can be provided as a lyophilized mixture with adjunct ingredients, or adjunct ingredients can be separately provided for combination by the user. Where a second antibody or antigen-binding fragment which binds HCA is employed, such antibody or fragment can be provided in the kit, for instance in a separate vial or container. The second antibody or fragment, if present, is typically labeled, and can be formulated in an analogous manner with the antibody or fragment formulations described above. The components (e.g., antibody, ancillary reagent) of the kit can be packaged separately or together within suitable containment means (e.g., bottle, box, envelope, tube). When the kit comprises a plurality of individually packaged components, the individual packages can be contained within a single larger containment means (e.g., bottle, box, envelope, tube). Since the HCA and anti-HCA antibody complex are heat sensitive, materials containing the HCA complex, all control sera, and all antibodies should be conveniently shipped in dry ice filled insulated containers, e.g., styrofoam containers.

In a particular embodiment, the kit comprises: (a) an immobilized antigen that is comprised of either HCA, epiglycanin, an idiotypic antibody (XII-24) to the detecting antibody (AE3 or AX2) or a surrogate antigen that has a similar affinity as HCA; (b) a suitable immobilized phase (e.g., micro titer plates, insoluble polymeric beads or particles) that can be washed and separated from a reaction mixture and are suitable for the immobilization of the an antibody or antigen; (c) a specific antibody (AX2 or AE3) with high affinity to HCA that can be detected using a detection method (e.g., radiation, colorimeteric, enzymatic, chemiluminecence, etc.), either directly or indirectly; (d) a series of calibration material (calibrators) comprised of materials that emulate HCA in patient samples that can be used to establish an appropriate response curve to map detection signal into concentration of HCA; and (e) any required blocking agents and buffers that inhibit nonspecific binding or any other signal generating reactions that are unrelated to HCA concentration. The calibrators of step (d) are stable over the useful lifetime of the kit.

In certain embodiments, this disclosure relates to kits for diagnosis of cancer. In one embodiment, the kit comprises an anti-idiotypic antibody or antigen-binding fragment thereof which binds to the variable region of an antibody that binds to HCA and suitable ancillary reagents. In certain embodiments, the kit further comprises an antibody that binds to HCA.

In certain embodiments, the kit comprises one or more of the following components: an anti-idiotypic antibody (XII-24) to the detecting antibody (AX2); a suitable immobilized phase (e.g., micro titer plates, insoluble polymeric beads or particles) that can be washed and separated from a reaction mixture and are suitable for the immobilization of an antibody disclosed herein; a specific antibody (AX2 or AE3) with high affinity to HCA that can be detected using a detection method (e.g., radiation, colorimeteric, enzymatic, chemiluminecence, etc.), either directly or indirectly; a series of calibration material (calibrators) comprised of materials that emulate HCA in patient samples that can be used to establish an appropriate response curve to map detection signal into concentration of HCA; and any required blocking agents and buffers that inhibit nonspecific binding or any other signal generating reactions that are unrelated to HCA concentration.

Examples

DOC (Detection of Carcinoma) Assay

A test sample having HCA typically contains autoantibody complexes that interferes with direct antibody measurements to HCA with an anti-HCA antibody such as AX2.

The HCA is present in the serum of cancer patients not as the free serum, but as the HCA-anti-HCA complex. Thus, a preferred assay method disclosed herein is to use an anti-idiotypic antibody such as XII-24 to break up these complexes and exposure to antibodies that directly bind HCA. Cleavage and binding reactions is likely a one step process.

Figure 2:
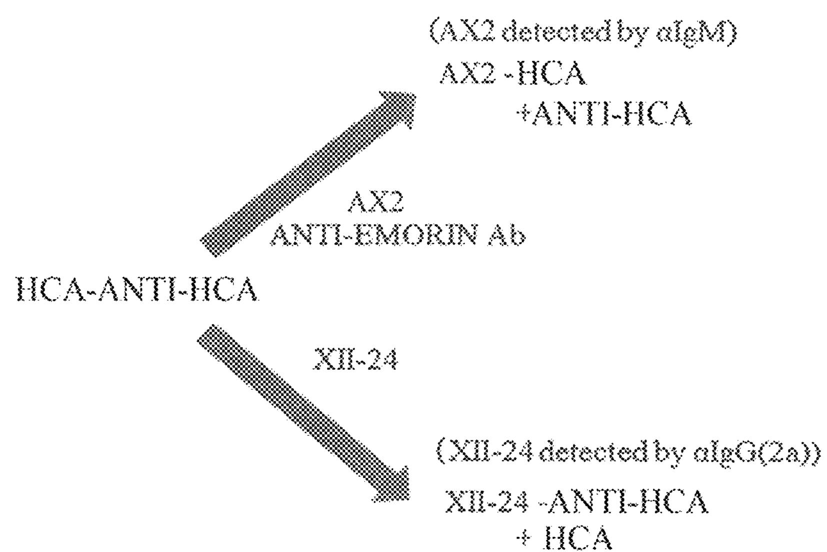
FIG. 2 illustrates the proposed HCA complex in a sample bound with potential autoantibodies (anti-HCA antibodies) that can interfere with detection methods. Although it is not intended that embodiments of this disclosure be limited by any particular mechanism, it is possible that exposure of a sample for testing the presence of HCA or Emorin with anti-idiotypic antibodies (XII-24) releases HCA to be further detected by anti-HCA/Emorin antibodies (AX2).

Cleavage made by the XII-24 antibody is illustrated in FIG. 2. A major reduction in the amount of interfering material occurs when the XII-24 antibody is used instead of direct exposure to AX2, as in the protocol below.

Disclosed is a robust and accurate assay, for use in the clinic, to detect, from 60 micro liters of blood, the presence of cancers of epithelial tissue (carcinomas) at either their early or late stages. Described herein is a competitive binding assay, which involves the use of two monoclonal antibodies derived from a cancer specific component, Emorin, of the epiglycanin glycoproteins. Emorin can be isolated from the epiglycanin mixture in two ways: size-exclusion chromatography and affinity chromatography.

The first monoclonal antibody, AX2, is produced by fusion of antibody-producing B cells from a C57BL mouse immunized with an epiglycanin carcinoma specific fraction (Emorin) and mouse myeloma (tumor) cells. This antibody is specific for the carcinoma-specific epitope in epiglycanin. It is an IgM.

The second monoclonal antibody was produced by the same general methodology. Immunization of a C57BL mouse was followed by fusion of the B cells from the spleen with mouse myeloma cells. The clone was selected for its specificity for the antibody-binding site (hypervariable region) in AX2. This antibody, XII-24, is an anti-idiotypic antibody. Immunologically it is similar in cancer specificity to Emorin. It is an IgG (2a) type antibody. FIG. 1 illustrates the relationship between the two antibodies and epiglycanin.

The rationale for producing an anti-idiotypic antibody resulted from the instability of Emorin. Both AX2 and XII-24 are quite stable, and this contributes to the robust character of the assay. The idiotypic activity of XII-24 enables binding from HCA to AX2, i.e., leaving the hypervariable region of XII-24 free to bind to the hypervariable region of AX2 on the plate.

The assay is performed in a 96-well immune plate (Immulon 2 B which is a high binding surface to provide increased binding of hydrophilic proteins and complexes). It consists of seven steps. Each step is performed on a rotary shaker at about 4° C. Each step is performed in the order as described below. Serum samples to be tested are kept frozen until thawed for use (then kept at 4° C.

Step 1. The wells are coated with a PBS solution (pH 7.75) containing AX2 antibody (125 ng per 100 μl per well) and the plate is incubated for 18-24 hours. The plate is washed 3 times (W3X). The procedure can be adapted for beads. In addition to the wells to be tested, each plate has wells reserved for control sera. Two wells: from a person without evidence of disease, zero present inhibition in the DOC assay and from a control patient with a documented carcinoma.

Step 2. To prevent additional non-specific absorption of the test sample, the wells in the plate with are further blocked by the addition of 250 μl of a solution of Aqua Block at 100% concentration (East Coast Bio, New Brunswick, Me.), and the plate is allowed to incubate for 2.0 hours. (W3X).

Step 3. In separate tubes the sera to be tested are incubated with the XII-24 antibody and neutralizing antibodies to remove interfering antibodies for 14-18 hours. The neutralizing antibodies are goat anti-mouse IgG(Fc) and goat anti-human IgG and lgM. During this period two events occur. One, the XII-24 in the wells cleaves the HCA-anti-HCA complex forming the XII-24-anti-HCA antibody complex and reducing the concentration of XII-24 available for binding to the AX2 on the plate. Two, the neutralizing antibodies eliminate the activity of the interfering antibodies from the serum.

Step 4. Each solution, which contained (if cancer the HCA-anti-HCA complex and the XII-24 antibody, and which now contains less of that antibody due to the XII-24's reaction with the complex) is added to its appropriate well (100 μl per well). Incubation is continued on the plate for 3-5 hours. (W3X). If no complex is present for the XII-24, which is an IgG(2a) antibody, to cleave (the control sample), all of the original XII-24 is now free to bind (by their hypervariable regions) to AX2 immobilized on the plate.

Step 5. A solution of biotin-labeled goat anti-mouse immunoglobulin IgG(2a) is added to each well (100 μl per well). The plate is incubated for 1.5 hours. (W3X). The biotin labeled antibody now binds to the XII-24 part of the XII-24-AX2 complex on the plate. This is the portion of the original XII-24 remaining after its reaction with the HCA-anti-HCA in the sample. However, if no HCA is in the sample (as in a normal sample), all of the original XII-24 will bind to AX2.

Step 6. A solution of 100 μl of horseradish peroxidase-labeled Streptavidin is added to each well. After an incubation of 60 minutes, the plate is washed 4 times. The streptavidin binds biotin. The plate is allowed to warm to ambient temperature Step 7. Following the addition of a solution of ABTS to each well, color develops in about 30 minutes. This is read in an automatic plate reader at 405 nm. If HCA is in the sera sample then the intensity of the signal will be reduced.

Below is a table wherein first row shows intensity data for samples from carcinoma (CA) (patients with prostate cancer) and sarcoma (SC) patients. The assay cannot differentiate between normal sarcomas, lymphomas, and leukemias, which are not cancers of epithelial tissue; thus, do not produce HCA. The sera from carcinoma patients have consistently lower absorbance values.

| SERUM | O.D. 405 | AVG. | % INHIB (SC 20) |
|---|---|---|---|
| CA 109 | 514, 496 | (505) | 20% |
| CA 110 | 526, 587 | (557) | 11% |
| SC 20 | 591, 665 | (628) | |
| SC 21 | 686, 792 | (739) | |
| DIL | 594, 607 | (601) | |

Each kit may be supplied with one serum from a known carcinoma patient in order to affirm that the assay is performing well. A kit may also include serum from an individual with no cancer or other pathological problems.

Levels of HCA During the Course of Cancer Treatment

Described is a protocol may be used to monitor HCA during chemotherapy. The HCA-anti-HCA complex may remain in the blood after the cancer is treated. Protocol 1) Draw blood (serum) from the patient and store frozen.

2) Administer excess humanized non-toxic AX2 intravenously. Wait overnight (left in the blood are AX2-HCA and anti-HCA).

3) Collect fresh serum. Perform the DOC Assay. The free HCA or HCA-anti-HCA (freshly secreted) binds to the XII-24 antibody.

The invention claimed is:

1. An anti-HCA antibody comprising the light and heavy chain CDRs of AX2 wherein, the light chain CDR1 comprises QDVGTA (SEQ ID NO: 11), CDR2 comprises WAST (SEQ ID NO: 12), and CDR3 and QHYINYPLT (SEQ ID NO: 13); and the heavy chain CDR1 comprises GYTFTEYT (SEQ ID NO: 14), CDR2 comprises FYPGSGSI (SEQ ID NO: 15), and CDR3 comprise ARGGYYDSFDN (SEQ ID NO: 16).

2. The antibody of claim 1, wherein the light chain comprises GIVMTQSHKFMSTSIGDRVSITCKASQDVGTAVAWYQQKPGQSPKLLIFWASTRHTGVPDRFTGSGSGTDFTLTISNVQSEDLADYFCQHYINYPLTFGAGTKLELK (SEQ ID NO: 9) or variant thereof with greater than 50% identity.

3. The antibody of claim 1, wherein the heavy chain comprises QVQLQQSGAELVKPGASVKLSCKASGYTFTEYTIHWVKQRSGQGLEWIGWFYPGSGSIKYNEKFKDKATLTADKYSSTVYMELSSLTSEDSAVYFCARGGYYDSFDNWGQGTTLTV SS (SEQ ID NO: 10) or variants thereof with greater than 50% identity.

4. The antibody of claim 1, conjugated to a label, fluorescent dye, quantum dot, nanoparticle, heterologous polypeptide, an enzyme, or solid surface.

5. A vector comprising a nucleic acid sequence encoding the antibody of claim 1 in operable combination with a promoter.

6. The vector of claim 5, wherein the promoter is a heterologous promoter, or the vector further encodes a selectable marker.

7. A host cell comprising the vector of claim 5.

8. A method of quantifying labeled anti-idiotypic antibodies capable of binding to an anti-HCA antibody and HCA complex after exposure to a sample comprising:

mixing a sample of blood with anti-idiotypic antibodies capable of binding that bind to an anti-HCA antibody and HCA complex in the sample antibodies providing a mixed sample, wherein the anti-idiotypic antibodies comprise the light and heavy chain CDRs of XII-24 wherein, the light chain CDR1 comprises QGISGN (SEQ ID NO: 3), CDR2 comprises HGTN (SEQ ID NO: 4), and CDR3 comprises VQYIQFPFT (SEQ ID NO: 5), and the heavy chain CDR1 comprises GYIFTDYY (SEQ ID NO: 6), CDR2 comprises IYPGSGNT (SEQ ID NO: 7), and CDR3 comprises ASSLYYPLDH (SEQ ID NO: 8);

mixing the mixed sample of blood with anti-HCA antibodies bound to a solid substrate providing immobilized anti-idiotypic antibodies and optionally immobilized HCA on the surface;

wherein the anti-HCA antibodies bound to the solid substrate comprise the light and heavy chain CDRs of AX2 wherein, the light chain CDR1 comprises QDVGTA (SEQ ID NO: 11), CDR2 comprises WAST (SEQ ID NO: 12), and CDR3 and QHYINYPLT (SEQ ID NO: 13), and the heavy chain CDR1 comprises GYTFTEYT (SEQ ID NO: 14), CDR2 comprises FYPGSGSI (SEQ ID NO: 15), and CDR3 comprise ARGGYYDSFDN (SEQ ID NO: 16);

labeling the immobilized anti-idiotypic antibodies providing a label on the surface; and quantitating the label on the surface.

9. A vector comprising a nucleic acid sequence encoding the light chain and the heavy chain of an anti-idiotypic antibody binding to an anti-epiglycanin antibody and in operable combination with a promoter, wherein the anti-idiotypic antibody comprises the light and heavy chain CDRs of XII-24 wherein, the light chain CDR1 comprises QGISGN (SEQ ID NO: 3), CDR2 comprises HGTN (SEQ ID NO: 4), and CDR3 comprises VQYIQFPFT (SEQ ID NO: 5); and the heavy chain CDR1 comprises GYIFTDYY (SEQ ID NO: 6), CDR2 comprises IYPGSGNT (SEQ ID NO: 7), and CDR3 comprises ASSLYYPLDH (SEQ ID NO: 8).

10. The vector of claim 9, wherein the promoter is a heterologous promoter, or the vector further encodes a selectable marker.

11. The vector of claim 9, wherein the light chain comprises DILMTQSPSSMSVSLGDTVSITCHASQGISGNIGWLQQKPGKSFKGLIYHGTNLEDGVPSRFSGSGSGADYSLTISSLESEDFADYYCVQYIQFPFTFGGGTKLEIKR (SEQ ID NO: 1) or variant thereof with greater than 50% identity.

12. The vector of claim 9, wherein the heavy chain comprises QVHLKQSGAEVVRPGASLKLSCKASGYIFTDYYVHWAKQRPGQGLEWIARIYPGSGNTYYNEKFMVKATLTAESSSSTAYMELSRLTSEDSAVYFCASSLYYPLDHWGQGTSVIVSS (SEQ ID NO: 2) or variants thereof with greater than 50% identity.

13. A host cell comprising the vector of claim 9.

* * * * *

SEQUENCE LISTING

```
<160> NUMBER OF SEQ ID NOS: 24

<210> SEQ ID NO 1
<211> LENGTH: 108
<212> TYPE: PRT
<213> ORGANISM: Artificial
<220> FEATURE:
<223> OTHER INFORMATION: Synthetic construct

<400> SEQUENCE: 1

Asp Ile Leu Met Thr Gln Ser Pro Ser Ser Met Ser Val Ser Leu Gly
1               5                   10                  15

Asp Thr Val Ser Ile Thr Cys His Ala Ser Gln Gly Ile Ser Gly Asn
            20                  25                  30

Ile Gly Trp Leu Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Ala Asp Tyr Ser Leu Thr Ile Ser Ser Leu Glu Ser
65                  70                  75                  80

Glu Asp Phe Ala Asp Tyr Tyr Cys Val Gln Tyr Ile Gln Phe Pro Phe
                85                  90                  95

Thr Phe Gly Gly Gly Thr Lys Leu Glu Ile Lys Arg
            100                 105


<210> SEQ ID NO 2
<211> LENGTH: 117
<212> TYPE: PRT
<213> ORGANISM: Artificial
<220> FEATURE:
<223> OTHER INFORMATION: Synthetic construct

<400> SEQUENCE: 2

Gln Val His Leu Lys Gln Ser Gly Ala Glu Val Val Arg Pro Gly Ala
1               5                   10                  15

Ser Leu Lys Leu Ser Cys Lys Ala Ser Gly Tyr Ile Phe Thr Asp Tyr
            20                  25                  30

Tyr Val His Trp Ala Lys Gln Arg Pro Gly Gln Gly Leu Glu Trp Ile
        35                  40                  45

Ala Arg Ile Tyr Pro Gly Ser Gly Asn Thr Tyr Tyr Asn Glu Lys Phe
    50                  55                  60

Met Val Lys Ala Thr Leu Thr Ala Glu Ser Ser Ser Ser Thr Ala Tyr
65                  70                  75                  80

Met Glu Leu Ser Arg Leu Thr Ser Glu Asp Ser Ala Val Tyr Phe Cys
                85                  90                  95

Ala Ser Ser Leu Tyr Tyr Pro Leu Asp His Trp Gly Gln Gly Thr Ser
            100                 105                 110

Val Ile Val Ser Ser
        115


<210> SEQ ID NO 3
<211> LENGTH: 6
<212> TYPE: PRT
<213> ORGANISM: Artificial
<220> FEATURE:
<223> OTHER INFORMATION: Synthetic construct

<400> SEQUENCE: 3

Gln Gly Ile Ser Gly Asn
1               5
```

<210> SEQ ID NO 4
<211> LENGTH: 4
<212> TYPE: PRT
<213> ORGANISM: Artificial
<220> FEATURE:
<223> OTHER INFORMATION: Synthetic construct

<400> SEQUENCE: 4

His Gly Thr Asn
1

<210> SEQ ID NO 5
<211> LENGTH: 9
<212> TYPE: PRT
<213> ORGANISM: Artificial
<220> FEATURE:
<223> OTHER INFORMATION: Synthetic construct

<400> SEQUENCE: 5

Val Gln Tyr Ile Gln Phe Pro Phe Thr
1               5

<210> SEQ ID NO 6
<211> LENGTH: 8
<212> TYPE: PRT
<213> ORGANISM: Artificial
<220> FEATURE:
<223> OTHER INFORMATION: Synthetic construct

<400> SEQUENCE: 6

Gly Tyr Ile Phe Thr Asp Tyr Tyr
1               5

<210> SEQ ID NO 7
<211> LENGTH: 8
<212> TYPE: PRT
<213> ORGANISM: Artificial
<220> FEATURE:
<223> OTHER INFORMATION: Synthetic construct

<400> SEQUENCE: 7

Ile Tyr Pro Gly Ser Gly Asn Thr
1               5

<210> SEQ ID NO 8
<211> LENGTH: 10
<212> TYPE: PRT
<213> ORGANISM: Artificial
<220> FEATURE:
<223> OTHER INFORMATION: Synthetic construct

<400> SEQUENCE: 8

Ala Ser Ser Leu Tyr Tyr Pro Leu Asp His
1               5                   10

<210> SEQ ID NO 9
<211> LENGTH: 107
<212> TYPE: PRT
<213> ORGANISM: Artificial
<220> FEATURE:
<223> OTHER INFORMATION: Synthetic construct

<400> SEQUENCE: 9

Gly Ile Val Met Thr Gln Ser His Lys Phe Met Ser Thr Ser Ile Gly
1               5                   10                  15

Asp Arg Val Ser Ile Thr Cys Lys Ala Ser Gln Asp Val Gly Thr Ala
20 25 30

Val Ala Trp Tyr Gln Gln Lys Pro Gly Gln Ser Pro Lys Leu Leu Ile
35 40 45

Phe Trp Ala Ser Thr Arg His Thr Gly Val Pro Asp Arg Phe Thr Gly
50 55 60

Ser Gly Ser Gly Thr Asp Phe Thr Leu Thr Ile Ser Asn Val Gln Ser
65 70 75 80

Glu Asp Leu Ala Asp Tyr Phe Cys Gln His Tyr Ile Asn Tyr Pro Leu
85 90 95

Thr Phe Gly Ala Gly Thr Lys Leu Glu Leu Lys
100 105

<210> SEQ ID NO 10
<211> LENGTH: 118
<212> TYPE: PRT
<213> ORGANISM: Artificial
<220> FEATURE:
<223> OTHER INFORMATION: Synthetic construct

<400> SEQUENCE: 10

Gln Val Gln Leu Gln Gln Ser Gly Ala Glu Leu Val Lys Pro Gly Ala
1 5 10 15

Ser Val Lys Leu Ser Cys Lys Ala Ser Gly Tyr Thr Phe Thr Glu Tyr
20 25 30

Thr Ile His Trp Val Lys Gln Arg Ser Gly Gln Gly Leu Glu Trp Ile
35 40 45

Gly Trp Phe Tyr Pro Gly Ser Gly Ser Ile Lys Tyr Asn Glu Lys Phe
50 55 60

Lys Asp Lys Ala Thr Leu Thr Ala Asp Lys Tyr Ser Ser Thr Val Tyr
65 70 75 80

Met Glu Leu Ser Ser Leu Thr Ser Glu Asp Ser Ala Val Tyr Phe Cys
85 90 95

Ala Arg Gly Gly Tyr Tyr Asp Ser Phe Asp Asn Trp Gly Gln Gly Thr
100 105 110

Thr Leu Thr Val Ser Ser
115

<210> SEQ ID NO 11
<211> LENGTH: 6
<212> TYPE: PRT
<213> ORGANISM: Artificial
<220> FEATURE:
<223> OTHER INFORMATION: Synthetic construct

<400> SEQUENCE: 11

Gln Asp Val Gly Thr Ala
1 5

<210> SEQ ID NO 12
<211> LENGTH: 4
<212> TYPE: PRT
<213> ORGANISM: Artificial
<220> FEATURE:
<223> OTHER INFORMATION: Synthetic construct

<400> SEQUENCE: 12

Trp Ala Ser Thr
1

<210> SEQ ID NO 13
<211> LENGTH: 9
<212> TYPE: PRT
<213> ORGANISM: Artificial
<220> FEATURE:
<223> OTHER INFORMATION: Synthetic construct

<400> SEQUENCE: 13

Gln His Tyr Ile Asn Tyr Pro Leu Thr
1 5

<210> SEQ ID NO 14
<211> LENGTH: 8
<212> TYPE: PRT
<213> ORGANISM: Artificial
<220> FEATURE:
<223> OTHER INFORMATION: Synthetic construct

<400> SEQUENCE: 14

Gly Tyr Thr Phe Thr Glu Tyr Thr
1 5

<210> SEQ ID NO 15
<211> LENGTH: 8
<212> TYPE: PRT
<213> ORGANISM: Artificial
<220> FEATURE:
<223> OTHER INFORMATION: Synthetic construct

<400> SEQUENCE: 15

Phe Tyr Pro Gly Ser Gly Ser Ile
1 5

<210> SEQ ID NO 16
<211> LENGTH: 11
<212> TYPE: PRT
<213> ORGANISM: Artificial
<220> FEATURE:
<223> OTHER INFORMATION: Synthetic construct

<400> SEQUENCE: 16

Ala Arg Gly Gly Tyr Tyr Asp Ser Phe Asp Asn
1 5 10

<210> SEQ ID NO 17
<211> LENGTH: 234
<212> TYPE: PRT
<213> ORGANISM: Artificial
<220> FEATURE:
<223> OTHER INFORMATION: Synthetic construct

<400> SEQUENCE: 17

Met Glu Thr His Ser Gln Val Phe Val Tyr Met Leu Leu Trp Leu Ser
1 5 10 15

Gly Val Glu Gly Gly Ile Val Met Thr Gln Ser His Lys Phe Met Ser
20 25 30

Thr Ser Ile Gly Asp Arg Val Ser Ile Thr Cys Lys Ala Ser Gln Asp
35 40 45

Val Gly Thr Ala Val Ala Trp Tyr Gln Gln Lys Pro Gly Gln Ser Pro
50 55 60

Lys Leu Leu Ile Phe Trp Ala Ser Thr Arg His Thr Gly Val Pro Asp
65 70 75 80

Arg Phe Thr Gly Ser Gly Ser Gly Thr Asp Phe Thr Leu Thr Ile Ser
85 90 95

```
Asn Val Gln Ser Glu Asp Leu Ala Asp Tyr Phe Cys Gln His Tyr Ile
            100                 105                 110

Asn Tyr Pro Leu Thr Phe Gly Ala Gly Thr Lys Leu Glu Leu Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Gly Glu Cys
225                 230


<210> SEQ ID NO 18
<211> LENGTH: 705
<212> TYPE: DNA
<213> ORGANISM: Artificial
<220> FEATURE:
<223> OTHER INFORMATION: Synthetic construct

<400> SEQUENCE: 18

atggagacac attctcaggt ctttgtatac atgttgctgt ggttgtctgg tgttgaagga     60

ggcattgtga tgacccagtc tcacaaattc atgtccacat caataggaga cagggtcagc    120

atcacctgca aggccagtca ggatgtgggt actgctgtgg cctggtatca acagaaacca    180

gggcaatctc ctaaactact gattttctgg gcatccaccc ggcacactgg agtccctgat    240

cgcttcacag gcagtggatc tgggacagat ttcactctca ccattagcaa tgtgcagtct    300

gaagacttgg cagattattt ctgtcagcat tatatcaact atcctctcac gttcggtgct    360

gggaccaagc tggagctgaa acgggctgat gctgcaccaa ctgtatccat cttcccacca    420

tccagtgagc agttaacatc tggaggtgcc tcagtcgtgt gcttcttgaa caacttctac    480

cccaaagaca tcaatgtcaa gtggaagatt gatggcagtg aacgacaaaa tggcgtcctg    540

aacagttgga ctgatcagga cagcaaagac agcacctaca gcatgagcag caccctcacg    600

ttgaccaagg acgagtatga acgacataac agctatacct gtgaggccac tcacaagaca    660

tcaacttcac ccattgtcaa gagcttcaac aggggagagt gttga                    705


<210> SEQ ID NO 19
<211> LENGTH: 592
<212> TYPE: PRT
<213> ORGANISM: Artificial
<220> FEATURE:
<223> OTHER INFORMATION: Synthetic construct

<400> SEQUENCE: 19

Met Glu Trp Cys Trp Val Phe Leu Phe Leu Leu Ser Val Thr Ala Gly
1               5                   10                  15

Val His Ser Gln Val Gln Leu Gln Gln Ser Gly Ala Glu Leu Val Lys
            20                  25                  30

Pro Gly Ala Ser Val Lys Leu Ser Cys Lys Ala Ser Gly Tyr Thr Phe
        35                  40                  45
```

```
Thr Glu Tyr Thr Ile His Trp Val Lys Gln Arg Ser Gly Gln Gly Leu
    50                  55                  60

Glu Trp Ile Gly Trp Phe Tyr Pro Gly Ser Gly Ser Ile Lys Tyr Asn
65                  70                  75                  80

Glu Lys Phe Lys Asp Lys Ala Thr Leu Thr Ala Asp Lys Tyr Ser Ser
                85                  90                  95

Thr Val Tyr Met Glu Leu Ser Ser Leu Thr Ser Glu Asp Ser Ala Val
            100                 105                 110

Tyr Phe Cys Ala Arg Gly Gly Tyr Tyr Asp Ser Phe Asp Asn Trp Gly
        115                 120                 125

Gln Gly Thr Thr Leu Thr Val Ser Ser Glu Ser Gln Ser Phe Pro Asn
    130                 135                 140

Val Phe Pro Leu Val Ser Cys Glu Ser Pro Leu Ser Asp Lys Asn Leu
145                 150                 155                 160

Val Ala Met Gly Cys Leu Ala Arg Asp Phe Leu Pro Ser Thr Ile Ser
                165                 170                 175

Phe Thr Trp Asn Tyr Gln Asn Asn Thr Glu Val Ile Gln Gly Ile Arg
            180                 185                 190

Thr Phe Pro Thr Leu Arg Thr Gly Gly Lys Tyr Leu Ala Thr Ser Gln
        195                 200                 205

Val Leu Leu Ser Pro Lys Ser Ile Leu Glu Gly Ser Asp Glu Tyr Leu
    210                 215                 220

Val Cys Lys Ile His Tyr Gly Gly Lys Asn Arg Asp Leu His Val Pro
225                 230                 235                 240

Ile Pro Ala Val Ala Glu Met Asn Pro Asn Val Asn Val Phe Val Pro
                245                 250                 255

Pro Arg Asp Gly Phe Ser Gly Pro Ala Pro Arg Lys Ser Lys Leu Ile
            260                 265                 270

Cys Glu Ala Thr Asn Phe Thr Pro Lys Pro Ile Thr Val Ser Trp Leu
        275                 280                 285

Lys Asp Gly Lys Leu Val Glu Ser Gly Phe Thr Thr Asp Pro Val Thr
    290                 295                 300

Ile Glu Asn Lys Gly Ser Thr Pro Gln Thr Tyr Lys Val Ile Ser Thr
305                 310                 315                 320

Leu Thr Ile Ser Glu Ile Asp Trp Leu Asn Leu Asn Val Tyr Thr Cys
                325                 330                 335

Arg Val Asp His Arg Gly Leu Thr Phe Leu Lys Asn Val Ser Ser Thr
            340                 345                 350

Cys Ala Ala Ser Pro Ser Thr Asp Ile Leu Thr Phe Thr Ile Pro Pro
        355                 360                 365

Ser Phe Ala Asp Ile Phe Leu Ser Lys Ser Ala Asn Leu Thr Cys Leu
    370                 375                 380

Val Ser Asn Leu Ala Thr Tyr Glu Thr Leu Asn Ile Ser Trp Ala Ser
385                 390                 395                 400

Gln Ser Gly Glu Pro Leu Glu Thr Lys Ile Lys Ile Met Glu Ser His
                405                 410                 415

Pro Asn Gly Thr Phe Ser Ala Lys Gly Val Ala Ser Val Cys Val Glu
            420                 425                 430

Asp Trp Asn Asn Arg Lys Glu Phe Val Cys Thr Val Thr His Arg Asp
        435                 440                 445

Leu Pro Ser Pro Gln Lys Lys Phe Ile Ser Lys Pro Asn Glu Val His
    450                 455                 460
```

-continued

```
Lys His Pro Pro Ala Val Tyr Leu Leu Pro Pro Ala Arg Glu Gln Leu
465                 470                 475                 480

Asn Leu Arg Glu Ser Ala Thr Val Thr Cys Leu Val Lys Gly Phe Ser
                485                 490                 495

Pro Ala Asp Ile Ser Val Gln Trp Leu Gln Arg Gly Gln Leu Leu Pro
            500                 505                 510

Gln Glu Lys Tyr Val Thr Ser Ala Pro Met Pro Glu Pro Gly Ala Pro
        515                 520                 525

Gly Phe Tyr Phe Thr His Ser Ile Leu Thr Val Thr Glu Glu Glu Trp
    530                 535                 540

Asn Ser Gly Glu Thr Tyr Thr Cys Val Val Gly His Glu Ala Leu Pro
545                 550                 555                 560

His Leu Val Thr Glu Arg Thr Val Asp Lys Ser Thr Gly Lys Pro Thr
                565                 570                 575

Leu Tyr Asn Val Ser Leu Ile Met Ser Asp Thr Gly Gly Thr Cys Tyr
            580                 585                 590


<210> SEQ ID NO 20
<211> LENGTH: 720
<212> TYPE: DNA
<213> ORGANISM: Artificial
<220> FEATURE:
<223> OTHER INFORMATION: Synthetic construct

<400> SEQUENCE: 20

atggaatggt gctgggtctt tctcttcctc ctgtcagtaa ctgcaggtgt ccactcccag      60

gtccaactgc agcagtctgg agctgagctg gtgaaacccg gggcatcagt gaagctgtcc     120

tgtaaggctt ctggctacac cttcactgaa tatactatac actgggtaaa gcagaggtct     180

ggacagggtc ttgaatggat tgggtggttt taccctggaa gtggtagtat aaagtataat     240

gagaaattca aggacaaggc cacattgact gcggacaaat actccagcac agtctatatg     300

gaacttagta gcttgacatc tgaagactct gcggtctatt tctgtgcaag agggggctac     360

tatgattctt ttgacaactg gggccaaggc accactctca cagtctcctc agagagtcag     420

tccttcccaa atgtcttccc cctcgtctcc tgcgagagcc ccctgtctga taagaatctg     480

gtggccatgg gctgcctagc ccgggacttc ctgcccagca ccatttcctt cacctggaac     540

taccagaaca acactgaagt catccagggt atcagaacct tcccaacact gaggacaggg     600

ggcaagtacc tagccacctc gcaggtgttg ctgtctccca agagcatcct tgaaggttca     660

gatgaatacc tggtatgcaa aatccactac ggaggcaaaa acagagatct gcatgtgccc     720


<210> SEQ ID NO 21
<211> LENGTH: 236
<212> TYPE: PRT
<213> ORGANISM: Artificial
<220> FEATURE:
<223> OTHER INFORMATION: Synthetic construct

<400> SEQUENCE: 21

Met Asp Met Met Val Leu Ala Gln Phe Leu Ala Phe Leu Leu Leu Trp
1               5                   10                  15

Phe Pro Gly Ala Arg Cys Asp Ile Leu Met Thr Gln Ser Pro Ser Ser
            20                  25                  30

Met Ser Val Ser Leu Gly Asp Thr Val Ser Ile Thr Cys His Ala Ser
        35                  40                  45

Gln Gly Ile Ser Gly Asn Ile Gly Trp Leu Gln Gln Lys Pro Gly Lys
    50                  55                  60
```

```
Ser Phe Lys Gly Leu Ile Tyr His Gly Thr Asn Leu Glu Asp Gly Val
65                  70                  75                  80

Pro Ser Arg Phe Ser Gly Ser Gly Ser Gly Ala Asp Tyr Ser Leu Thr
                85                  90                  95

Ile Ser Ser Leu Glu Ser Glu Asp Phe Ala Asp Tyr Tyr Cys Val Gln
            100                 105                 110

Tyr Ile Gln Phe Pro Phe Thr Phe Gly Gly Gly Thr Lys Leu Glu Ile
        115                 120                 125

Lys Arg Ala Asp Ala Ala Pro Thr Val Ser Ile Phe Pro Pro Ser Ser
    130                 135                 140

Glu Gln Leu Thr Ser Gly Gly Ala Ser Val Val Cys Phe Leu Asn Asn
145                 150                 155                 160

Phe Tyr Pro Lys Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
            180                 185                 190

Ser Thr Tyr Ser Met Ser Ser Thr Leu Thr Leu Thr Lys Asp Glu Tyr
        195                 200                 205

Glu Arg His Asn Ser Tyr Thr Cys Glu Ala Thr His Lys Thr Ser Thr
    210                 215                 220

Ser Pro Ile Val Lys Ser Phe Asn Arg Gly Glu Cys
225                 230                 235
```

<210> SEQ ID NO 22
<211> LENGTH: 711
<212> TYPE: DNA
<213> ORGANISM: Artificial
<220> FEATURE:
<223> OTHER INFORMATION: Synthetic construct

<400> SEQUENCE: 22

```
atggacatga tggtccttgc tcagtttctt gcattcttgt tgctttggtt tccaggtgca     60

agatgtgaca tcctgatgac ccaatctcca tcctccatgt ctgtatctct gggagacaca    120

gtcagcatca cttgccatgc aagtcaaggc attagcggta atatagggtg gttgcagcag    180

aaaccaggga aatcatttaa gggcctgatc tatcatggaa ccaacttgga agatggagtt    240

ccatcaaggt tcagtggcag tggatctgga gcagattatt ctctcaccat cagcagccta    300

gaatctgaag attttgcaga ttattactgt gtacagtaca ttcagtttcc gttcacgttc    360

ggaggggggga ccaagctgga gataaaacgg gctgatgctg caccaactgt atccatcttc    420

ccaccatcca gtgagcagtt aacatctgga ggtgcctcag tcgtgtgctt cttgaacaac    480

ttctacccca aagacatcaa tgtcaagtgg aagattgatg gcagtgaacg acaaaatggc    540

gtcctgaaca gttggactga tcaggacagc aaagacagca cctacagcat gagcagcacc    600

ctcacgttga ccaaggacga gtatgaacga cataacagct atacctgtga ggccactcac    660

aagacatcaa cttcacccat tgtcaagagc ttcaacaggg gagagtgttg a             711
```

<210> SEQ ID NO 23
<211> LENGTH: 466
<212> TYPE: PRT
<213> ORGANISM: Artificial
<220> FEATURE:
<223> OTHER INFORMATION: Synthetic construct

<400> SEQUENCE: 23

```
Met Gly Trp Ser Trp Ile Phe Phe Phe Leu Leu Ser Gly Thr Ala Gly
```

-continued

```
1               5                   10                  15

Val His Cys Gln Val His Leu Lys Gln Ser Gly Ala Glu Val Val Arg
            20                  25                  30

Pro Gly Ala Ser Leu Lys Leu Ser Cys Lys Ala Ser Gly Tyr Ile Phe
        35                  40                  45

Thr Asp Tyr Tyr Val His Trp Ala Lys Gln Arg Pro Gly Gln Gly Leu
    50                  55                  60

Glu Trp Ile Ala Arg Ile Tyr Pro Gly Ser Gly Asn Thr Tyr Tyr Asn
65                  70                  75                  80

Glu Lys Phe Met Val Lys Ala Thr Leu Thr Ala Glu Ser Ser Ser Ser
                85                  90                  95

Thr Ala Tyr Met Glu Leu Ser Arg Leu Thr Ser Glu Asp Ser Ala Val
            100                 105                 110

Tyr Phe Cys Ala Ser Ser Leu Tyr Tyr Pro Leu Asp His Trp Gly Gln
        115                 120                 125

Gly Thr Ser Val Ile Val Ser Ser Ala Lys Thr Thr Ala Pro Ser Val
    130                 135                 140

Tyr Pro Leu Ala Pro Val Cys Gly Asp Thr Thr Gly Ser Ser Val Thr
145                 150                 155                 160

Leu Gly Cys Leu Val Lys Gly Tyr Phe Pro Glu Pro Val Thr Leu Thr
                165                 170                 175

Trp Asn Ser Gly Ser Leu Ser Ser Gly Val His Thr Phe Pro Ala Val
            180                 185                 190

Leu Gln Ser Asp Leu Tyr Thr Leu Ser Ser Ser Val Thr Val Thr Ser
        195                 200                 205

Ser Thr Trp Pro Ser Gln Ser Ile Thr Cys Asn Val Ala His Pro Ala
    210                 215                 220

Ser Ser Thr Lys Val Asp Lys Lys Ile Glu Pro Arg Gly Pro Thr Ile
225                 230                 235                 240

Lys Pro Cys Pro Pro Cys Lys Cys Pro Ala Pro Asn Leu Leu Gly Gly
                245                 250                 255

Pro Ser Val Phe Ile Phe Pro Pro Lys Ile Lys Asp Val Leu Met Ile
            260                 265                 270

Ser Leu Ser Pro Ile Val Thr Cys Val Val Val Asp Val Ser Glu Asp
        275                 280                 285

Asp Pro Asp Val Gln Ile Ser Trp Phe Val Asn Asn Val Glu Val His
    290                 295                 300

Thr Ala Gln Thr Gln Thr His Arg Glu Asp Tyr Asn Ser Thr Leu Arg
305                 310                 315                 320

Val Val Ser Ala Leu Pro Ile Gln His Gln Asp Trp Met Ser Gly Lys
                325                 330                 335

Glu Phe Lys Cys Lys Val Asn Asn Lys Asp Leu Pro Ala Pro Ile Glu
            340                 345                 350

Arg Thr Ile Ser Lys Pro Lys Gly Ser Val Arg Ala Pro Gln Val Tyr
        355                 360                 365

Val Leu Pro Pro Pro Glu Glu Glu Met Thr Lys Lys Gln Val Thr Leu
    370                 375                 380

Thr Cys Met Val Thr Asp Phe Met Pro Glu Asp Ile Tyr Val Glu Trp
385                 390                 395                 400

Thr Asn Asn Gly Lys Thr Glu Leu Asn Tyr Lys Asn Thr Glu Pro Val
                405                 410                 415

Leu Asp Ser Asp Gly Ser Tyr Phe Met Tyr Ser Lys Leu Arg Val Glu
            420                 425                 430
```

-continued

```
Lys Lys Asn Trp Val Glu Arg Asn Ser Tyr Ser Cys Ser Val Val His
        435                 440                 445

Glu Gly Leu His Asn His His Thr Thr Lys Ser Phe Ser Arg Thr Pro
    450                 455                 460

Gly Lys
465


<210> SEQ ID NO 24
<211> LENGTH: 900
<212> TYPE: DNA
<213> ORGANISM: Artificial
<220> FEATURE:
<223> OTHER INFORMATION: Synthetic construct

<400> SEQUENCE: 24

atgggatgga gctggatctt tttcttcctc ctgtcaggaa ctgcaggtgt ccactgtcag      60

gtccacctga agcagtctgg ggctgaggtg gtgaggcctg gggcttcatt gaaactgtcc     120

tgcaaggctt ctggctacat tttcactgac tactatgtgc actgggcgaa acagcggcct     180

ggacagggac ttgagtggat tgcaaggatt tatcctggaa gtggtaatac ttactacaat     240

gagaaattca tggtcaaggc cacactgaca gcagaatcct cctccagcac tgcctacatg     300

gagctcagta ggctgacatc tgaggactct gctgtctatt tttgtgcaag cagcctctat     360

tatcctttgg accactgggg tcaaggaacc tcagtcatcg tctcctcagc caaaacaaca     420

gccccatcgg tctatccact ggcccctgtg tgtggagata caactggctc ctcggtgact     480

ctaggatgcc tggtcaaggg ttatttccct gagccagtga ccttgacctg gaactctgga     540

tccctgtcca gtggtgtgca caccttccca gctgtcctgc agtctgacct ctacaccctc     600

agcagctcag tgactgtaac ctcgagcacc tggcccagcc agtccatcac ctgcaatgtg     660

gcccacccgg caagcagcac caaggtggac aagaaaattg agcccagagg gcccacaatc     720

aagccctgtc ctccatgcaa atgcccagca cctaacctct tgggtggacc atccgtcttc     780

atcttccctc caaagatcaa ggatgtactc atgatctccc tgagccccat agtcacatgt     840

gtggtggtgg atgtgagcga ggatgaccca gatgtccaga tcagctggtt tgtgaacaac     900
```